United States Patent
Mehanian et al.

(10) Patent No.: US 11,446,004 B2
(45) Date of Patent: Sep. 20, 2022

(54) ULTRASOUND SYSTEMS AND METHODS OF IDENTIFYING FLUIDS IN BODY REGIONS USING THE SAME

(71) Applicant: Tokitae LLC, Bellevue, WA (US)

(72) Inventors: Courosh Mehanian, Redmond, WA (US); Sebastian Wachsmann-Hogiu, Montreal (CA); Benjamin K. Wilson, Snoqualmie, WA (US); Xinliang Zheng, Issaquah, WA (US)

(73) Assignee: Tokitae LLC, Bellevue, WA (US)

( * ) Notice: Subject to any disclaimer, the term of this patent is extended or adjusted under 35 U.S.C. 154(b) by 1038 days.

(21) Appl. No.: 15/985,808

(22) Filed: May 22, 2018

(65) Prior Publication Data
US 2018/0353156 A1  Dec. 13, 2018

Related U.S. Application Data

(60) Provisional application No. 62/517,662, filed on Jun. 9, 2017.

(51) Int. Cl.
*A61B 8/00* (2006.01)
*A61B 8/08* (2006.01)
(Continued)

(52) U.S. Cl.
CPC ............ *A61B 8/4444* (2013.01); *A61B 8/085* (2013.01); *A61B 8/0833* (2013.01);
(Continued)

(58) Field of Classification Search
CPC ..... A61B 5/0066; A61B 8/4483; A61B 3/102; A61B 8/467; A61B 8/08; A61B 8/5223; A61B 8/12; A61B 5/4878; A61B 5/08; A61B 5/0031; A61B 8/4488; A61B 8/5269; A61B 8/0833; A61B 8/4444; A61B 8/085; A61B 8/54; A61B 8/5246; G06T 7/0012; G06T 2207/10101; G16H 50/30; G01S 7/5206; G01S 15/8915
See application file for complete search history.

(56) References Cited

U.S. PATENT DOCUMENTS 5,574,212 A * 11/1996 Madsen ................ G01S 7/5205
                                                              73/618
9,848,852 B2 * 12/2017 Hancock ................ A61B 8/445
(Continued)

FOREIGN PATENT DOCUMENTS

| KR | 10-2016-0053552 A | 5/2016 |
|---|---|---|
| WO | 2014195742 A1 | 12/2014 |
| WO | 2016098929 A1 | 6/2016 |

OTHER PUBLICATIONS

PCT International Search Report; International App. No. PCT/US2018/036394; dated Sep. 11, 2018; pp. 1-3.
(Continued)

*Primary Examiner* — Baisakhi Roy
(74) *Attorney, Agent, or Firm* — AEON Law, PLLC; Adam L. K. Philipp; Shan Liao

(57) ABSTRACT

Embodiments disclosed herein are directed to systems and methods for determining if a fluid is present in a body region. The systems and methods include using ultrasound systems having operational parameters that provide ultrasound echo maps having high resolution B-line artefacts.

9 Claims, 12 Drawing Sheets

(51) Int. Cl.
*G01S 7/52* (2006.01)
*G01S 15/89* (2006.01)
*A61B 8/14* (2006.01)
*A61B 5/00* (2006.01)

(52) U.S. Cl.
CPC .......... *A61B 8/4483* (2013.01); *A61B 8/4488* (2013.01); *A61B 8/5246* (2013.01); *A61B 8/5269* (2013.01); *A61B 8/54* (2013.01); *G01S 7/5206* (2013.01); *G01S 15/8915* (2013.01); *A61B 5/7264* (2013.01); *A61B 8/14* (2013.01); *G01S 7/52047* (2013.01)

(56) References Cited

U.S. PATENT DOCUMENTS

| | | | |
|---|---|---|---|
| 2008/0008605 A1 | 1/2008 | Bauer et al. | |
| 2008/0086055 A1 | 4/2008 | Sakai et al. | |
| 2009/0036777 A1* | 2/2009 | Zhang | A61B 8/12 600/459 |
| 2013/0023767 A1* | 1/2013 | Mammone | A61B 8/14 600/440 |
| 2015/0002538 A1 | 1/2015 | Sohn et al. | |
| 2015/0150503 A1* | 6/2015 | Pamnani | A61B 8/543 600/438 |
| 2015/0271586 A1* | 9/2015 | Fukuzawa | G01L 9/0051 381/122 |
| 2015/0348287 A1* | 12/2015 | Yi | G06F 17/13 382/131 |
| 2016/0143617 A1* | 5/2016 | Ebbini | G01S 15/8915 600/447 |
| 2016/0239959 A1* | 8/2016 | Blackbourne | G06T 7/0012 |
| 2016/0287217 A1* | 10/2016 | Mueller | A61B 8/467 |
| 2016/0307314 A1* | 10/2016 | Reisman | A61B 5/7425 |
| 2017/0086790 A1 | 3/2017 | Halmann et al. | |
| 2018/0078143 A1* | 3/2018 | Pramanik | A61B 5/0095 |
| 2018/0242844 A1* | 8/2018 | Liu | A61B 3/102 |
| 2018/0344293 A1* | 12/2018 | Raju | A61B 8/5276 |
| 2018/0353156 A1* | 12/2018 | Mehanian | A61B 8/4483 |

OTHER PUBLICATIONS

Peng et al.; "Classification of Pulmonary Emphysema in CT Images Based on Multi-Scale Deep Convolutional Neural Networks"; ICIP; 2018; pp. 3119-3123; IEEE.

Peng et al.; "Joint Weber-Based Rotation invariant Uniform Local Ternary Pattern for Classification of Pulmonary Emphysema in CT Images"; ICIP; 2017; pp. 2050-2054; IEEE.

Peng et al.; "Multi-scale Residual Network with Two Channels of Raw CT Image and Its Differential Excitation Component for Emphysema Classification"; DLMIA 2018/ML-CDS 2018 LNCS 11045; pp. 36-46: Springer Nature Switzerland AG 2018.

Anderson et al., "Inter-Rater Reliability of Quantifying Pleural B-Lines Using Multiple Counting Methods", Journal of Ultrasound in Medicine, vol. 32, No. 1, Jan. 2013, pp. 115-120.

Extended European Search Report; EP Application No. 18814338.2; dated Jan. 27, 2021, 12 pages.

Sperandeo et al., "Transthoracic Ultrasound in the Assessment of Pleural and Pulmonary Diseases: Use and Limitations", La Radiologia Medica, vol. 119, No. 10, Oct. 2014, pp. 729-740.

Volpicelli et al., "Usefulness of Lung Ultrasound in the Bedside Distinction Between Pulmonary Edema and Exacerbation of COPD", Emergency Radiology, vol. 15, No. 3, 2008, pp. 145-151.

* cited by examiner

ULTRASOUND SYSTEMS AND METHODS OF IDENTIFYING FLUIDS IN BODY REGIONS USING THE SAME

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc., applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)).

PRIORITY APPLICATIONS

The present application claims benefit of priority of United States Provisional Patent Application No. 62/517,662, entitled ULTRASOUND SYSTEMS AND METHODS OF IDENTIFYING FLUIDS IN BODY REGIONS USING THE SAME, naming COUROSH MEHANIAN, SEBASTIAN WACHSMANN-HOGIU, BENJAMIN K. WILSON, AND XINLIANG ZHENG as inventors, filed 9 Jun. 2017, which was filed within the twelve months preceding the filing date of the present application or is an application of which a currently co-pending priority application is entitled to the benefit of the filing date.

This invention is made with Government support under Agreement No. HR0011-17-3-001, awarded by DARPA. The Government has certain rights in the invention.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Ultrasound radiation can be used to probe tissues to identify body structures within a body. Ultrasound probes typically include an ultrasound transducer that emits and detects ultrasound radiation.

Ultrasound probes/transducers can have various designs and can come in linear and curvilinear configurations. In linear configurations an array of ultrasound elements may be arranged in a substantially linear or planar arrangement within an ultrasound probe. Such linear ultrasound transducer arrays may provide a pleural line and zero or more A-line artefacts that are substantially linear and horizontal on an echo map, while also providing B-line artefacts that are substantially linear and vertically oriented on an echo map. In curvilinear configurations an array of ultrasound elements may be arranged in a substantially curved, domed, or arcuate arrangement within an ultrasound probe. Such curvilinear ultrasound transducer arrays may provide a pleural line and A-line artefacts that are substantially arcuate and horizontally arranged on an echo map, while also providing B-line artefacts that are substantially linear (radially expanding or comet-tailed) and substantially vertically oriented on an echo map.

As ultrasound radiation is emitted into a body structure, the ultrasound radiation may reflect or scatter off of one or more portions of the body structure or region and return to the ultrasound probe or transducer. This returned ultrasound radiation may be received and processed to indicate the spatial arrangement of the body structure, such as a depth of a lung wall or lesion within a body. B-line artefacts may indicate that a fluid is present in a body structure, but may not be readily discernable in standard ultrasound probes (e.g., scans).

Therefore, developers and users of ultrasound systems continue to seek improvements to ultrasound systems and diagnostic techniques for use in determining a presence of fluid in body regions.

SUMMARY

Embodiments disclosed herein relate to systems and methods for producing and using ultrasound echo maps for determining the presence of a fluid in a body structure.

In an embodiment, a system for determining a presence of fluid in a body structure is disclosed. The system includes an ultrasound transducer including a plurality of ultrasonic elements, the ultrasound transducer configured to emit ultrasound radiation and receive returned ultrasound radiation. The system includes a computing device operably coupled to the ultrasound transducer. The computing device includes memory and a processor operably coupled thereto. The memory includes one or more operational programs stored thereon. The processor is configured to access and execute the one or more operational programs. The one or more operational programs include machine readable and executable instructions for automatically controlling a plurality of parameters of the ultrasound transducer for causing the ultrasound transducer to emit the ultrasound radiation at a frequency below about 15 MHz and to receive the returned ultrasound radiation and to assemble electrical signals output from the plurality of ultrasonic elements to provide an ultrasound echo map having one or more B-lines that include a signal-to-noise ratio of at least 2.

In an embodiment, a method for determining a presence of fluid in a body region is disclosed. The method includes emitting ultrasound radiation at a frequency below about 15 MHz into a body region from an ultrasound transducer having a plurality of ultrasonic elements. The method includes controlling one or more properties of the ultrasound radiation with a computing device operably coupled to the ultrasound transducer. The computing device includes a memory and processor operably coupled to the memory. The memory includes one or more operational programs having machine readable and executable instructions for controlling the ultrasound transducer. The method further includes receiving returned ultrasound radiation returned from the body region with the ultrasound transducer. The method also includes generating, with the computing device, an ultrasound echo map with the returned ultrasound radiation that includes one or more B-lines having a signal-to-noise ratio of at least 2.

In an embodiment, a method for determining a presence of fluid in a body region is disclosed. The method includes emitting ultrasound radiation at a frequency below about 15 MHz into a body region from an ultrasound transducer having a plurality of ultrasonic elements. The method includes controlling one or more properties of the ultrasound radiation with a computing device operably coupled to the ultrasound transducer by actuating a B-line mode operational program. The computing device includes a memory and processor operably coupled to the memory. The memory includes one or more operational programs having machine readable and executable instructions for controlling the ultrasound transducer. The one or more operational programs include at least one B-line mode operational program and at least one non-B-line mode operational program. The method includes receiving returned ultrasound radiation from the body region with the ultrasound transducer. The method includes generating, with the computing device, an ultrasound echo map with the returned ultrasound radiation that includes one or more B-lines having a signal-to-noise ratio of at least 2.

In an embodiment, a non-transitory computer readable medium including one or more machine readable instructions stored thereon that when executed by a computing device, perform a method is disclosed. The one or more machine readable instructions stored thereon may include one or more portions of any of the methods disclosed herein.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to illustrating aspects, embodiments, and features described above, further aspects, embodiments, and features will become apparent by reference to the drawings and the following detailed description.

DETAILED DESCRIPTION

Figure 1:
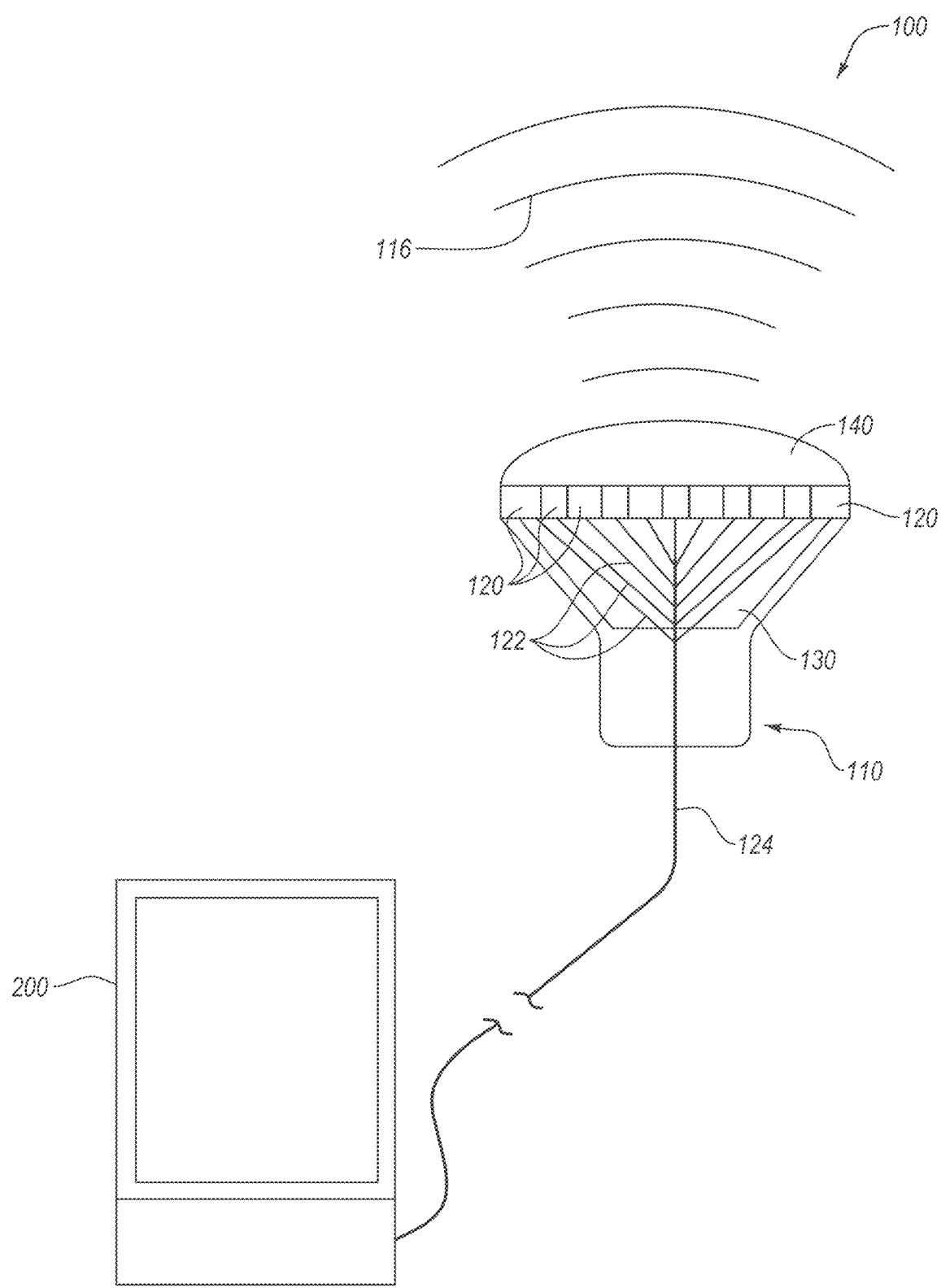
FIG. 1 is a schematic illustration of an ultrasound imaging system, according to an embodiment.

Embodiments disclosed herein relate to ultrasound imaging systems, and methods of using the same. The ultrasound echo maps (e.g., ultrasound image or sonogram) disclosed herein include images or spatially arranged sets of data (e.g., returned ultrasound radiation intensities or received radio frequency intensities) in any computer readable format, such as png, jpeg, gif, tiff, bmp, or any other suitable file type. The ultrasound systems and related methods herein provide reliable ultrasound echo maps of regions within a body through one or more body structures, such as a rib cage and/or lungs. The systems and methods herein can identify fluids in regions within a body (e.g., body structure or region), such as fluid in a lung, by providing selective B-line operating conditions from an ultrasound transducer and associated computing device. B-lines appear on echo maps at high acoustic impedance mismatch interfaces (e.g., a tissue/air interface such as in alveoli in lungs). As explained in more detail below, a pleural line and A-lines are generally arranged as laterally extending structures in an ultrasound echo map while B-lines are generally arranged as longitudinally extending structures substantially orthogonal to the a pleural line and A-lines. The pleural line typically indicates a body structure such as a wall of a lung or uterus, while B-lines typically indicate a fluid within a body structure having an impedance mismatch (e.g., a fluid at a tissue/air interface such a lung).

The ultrasound systems herein can accurately identify a presence of a fluid within a body, body structure, or body region, such as a lung. For example, the presence of fluid in a lung may be indicative of the subject having pneumonia. The systems and methods disclosed herein can automatically emit ultrasound radiation (e.g., ultrasound energy) having one or more properties that provide high resolution of B-lines (e.g., high contrast and/or high sensitivity to B-lines) in ultrasound echo maps, and receive returned ultrasound radiation. The returned ultrasound radiation (e.g., reflected ultrasound radiation, scattered ultrasound radiation, or ultrasound echoes) may provide high resolution of B-lines in ultrasound echo maps. Accordingly, highly trained sonographers or other medical professionals may not be required to determine if a subject has fluid in their lungs (or another body region having an impedance mismatch) using an ultrasound probe/transducer. The systems and methods therein may enable ultrasound system operators to detect fluid in body regions at a performance level equal to or better than a highly-trained sonographer or doctor, such as by selecting a B-line mode of operation. The systems and methods disclosed herein provide a comprehensive ultrasound tool, which uses a computing system to automatically control the emission of ultrasound radiation to include specific selected properties and to control the reception of returned ultrasound radiation to provide ultrasound echo maps having high resolution B-line structures therein. A used herein, the term high resolution refers to sensitivity to B-line structures that results in B-line structures in echo maps that have any of the signal-to-noise ratios, sharpness ratios, or maximized combinations thereof disclosed herein.

FIG. 1 is a schematic illustration of an ultrasound imaging system 100, according to an embodiment. The ultrasound imaging system 100 includes an ultrasound transducer 110 and a computing system 200 operably coupled to the ultrasound transducer 110. The ultrasound transducer 110 may include a plurality of ultrasonic elements 120 for emitting ultrasound radiation and receiving returned ultrasound radiation. The plurality of ultrasound elements 120 may be arranged in a linear array, a curvilinear array, or any other suitable array arrangement. In some embodiments, the plurality of ultrasound elements 120 may be backed by a damping block 130 or material. The damping block 130 may include a material that dampens or absorbs ultrasound radiation. The damping block 130 may be disposed on the back side of the transducer element(s) (e.g., on an inward facing side of the ultrasonic elements 120). In some embodiments, each of the plurality of ultrasonic elements 120 may be operably coupled to a power supply (not shown), such as via individual electrical connections 122. For example, the individual electrical connections 122 may include one or more of electrical leads or wires, a circuit board, or electrical pins. In some embodiments, the individual electrical connections 122 may form at least a portion of an electrical connection 124 to a power supply and/or the computing device 200. The ultrasound transducer 110 may include at least one matching layer 140 disposed on top of the plurality of ultrasonic elements 120. The at least one matching layer 140 may include one or more layers of materials having an acoustic impedance value that is between that of the ultrasonic elements 120 and tissue of a subject (e.g., organ tissue, bone, vessel tissue, etc.). The properties of the ultrasound radiation 116 emitted by the ultrasound transducer 110 may be selectively controlled by the computing device 200.

As explained in more detail below, the computing device 200 may include a memory and a processor operably coupled thereto. The computing device 200 may be programmed to control one or more of a power output of the ultrasound transducer (e.g., ultrasound radiation intensity), a number of ultrasonic elements used to emit and/or receive ultrasound radiation in the ultrasound transducer, an ultrasound beam form, an ultrasound beam focal depth, an ultrasound radiation frequency, a dynamic range of the ultrasound radiation, etc. The computing device 200 may include one or more of a user input and a display. The user input may be used to receive input from a user, provide input (e.g., operational instructions) to the ultrasound transducer 110, retrieve data detected with the ultrasound transducer 110, display one or more ultrasound echo maps (e.g., ultra sound images or sonograms), input or select selected properties of ultrasound radiation; input or select a mode of operation for the ultrasound transducer, activate the system 100, etc. The display may be used to view an operational status of the system 100, view current properties or parameters of the ultrasound radiation being emitted, view an ultrasound echo map, etc.

In some embodiments, the plurality of ultrasonic elements 120 may include piezoelectric ultrasound elements or transducers, or any other suitable transducer element for emitting ultrasound radiation (e.g., energy) responsive to an electrical input, and, emitting an electrical output responsive to receiving ultrasound input (e.g., returned ultrasound radiation such as reflected and/or scatter ultrasound radiation). For example, the plurality of ultrasonic elements 120 may include piezoelectric transducers, which can emit ultrasound radiation according or responsive to an electrical stimulus provided thereto (e.g., emit ultrasound radiation responsive to an amount of electricity provided thereto), and can provide an electrical stimulus according or responsive to a mechanical stimulus provided thereto (e.g., provide an electrical signal responsive to receiving mechanical pressure from returned ultrasound radiation). In some embodiments, the plurality of ultrasound elements 120 may include a material composed to emit and receive ultrasound radiation, such as quartz crystal, lead-zirconate-titanate, any other suitable piezoelectric material for producing and receiving ultrasound radiation, or combinations thereof. In some embodiments, the plurality of ultrasonic elements 120 may be configured to emit and/or receive any of the ultrasound radiation frequencies, powers, waveforms, etc. disclosed herein. For example, the plurality of ultrasonic elements 120 may be configured to selectively emit ultrasound radiation at a frequency below about 15 MHz.

In some embodiments, the plurality of ultrasonic elements 120 may be arranged in linear arrays, curvilinear arrays, or a phased array. Depending upon the arrangement of the array of ultrasonic elements 120, a resulting ultrasound echo map may include substantially linear features (e.g., substantially linear pleural lines and/or A-lines and/or substantially linear B-lines) for a linear array or substantially arcuate and radially expanding features (e.g., arcuate pleural lines and/or A-line artefacts and radially expanding or comet-tailed B-lines) for curvilinear arrays. In some embodiments, the plurality of ultrasonic elements 120 may be arranged as a phased array. In some embodiments, the plurality of ultrasonic elements 120 may include at least 2 ultrasonic elements, such as about 2 to about 100 ultrasonic elements, about 5 to about 550 ultrasonic elements, about 10 to about 260 ultrasonic elements, about 2 to about 256 ultrasonic elements, about 100 to about 550 ultrasonic elements, about 50 to about 150 ultrasonic elements, about 32 to about 128 ultrasonic elements, about 32 to about 256 ultrasonic elements, about 128 to about 256 ultrasonic elements, about 250 to about 550 ultrasonic elements, more than about 20 ultrasonic elements, more than about 125 ultrasonic elements, less than about 550 ultrasonic elements, less than about 56 elements, or less than about 128 ultrasonic elements. The plurality of ultrasonic elements 120 may be arranged in an array, wherein each of the plurality of ultrasonic elements 120 is disposed adjacent to another of the plurality of ultrasonic elements 120. Each of the plurality of ultrasonic elements 120 in the array may be individually controllable, such as via the computing device 200, to selectively control properties of the ultrasound radiation emitted therefrom and/or the number of ultrasonic elements 120 that receive returned ultrasound radiation (e.g. or report the received ultrasound radiation to the computing device). For example, the computing device 200 may be operably coupled to a power supply (not shown) and may control an electrical input to each of the plurality of ultrasonic elements 120 via the individual electronic connections 122. For example, the computing device 200 may selectively control a power of the ultrasound radiation emitted from at least some of the plurality of ultrasonic elements 120, a number of the plurality of ultrasonic elements 120 in an array that emit ultrasound radiation 116, a frequency of the ultrasound radiation emitted, or any other properties of the ultrasound radiation or operation of the ultrasound transducer 110 as controlled via the individual electronic connections 122. For example, each of the plurality of ultrasonic elements 120 may be operably coupled to a power supply (not shown) via a respective one of the individual electrical connections 122, such that each of the ultrasonic elements 120 may be selectively controllable via the individual electrical connections 122.

The damping block 130 may include a material composed to limit or dampen vibrations in the transducer 110, such as to provide reliable emission and reception of ultrasonic radiation/energy. The damping block 130 may include a polymer, an epoxy, a metal, a ceramic, a composite, a metal powder (e.g., gold, silver, tungsten, etc.), mixtures of any of the foregoing (e.g., tungsten powder/epoxy composite), or any other damping material. The damping block 130 may extend away from the plurality of ultrasonic elements 120 to a point within the ultrasound transducer 110. In some embodiments, the individual electrical connections 122 may be embedded in or otherwise travel through the damping block 130.

The at least one matching layer 140 may include one or more layers of materials having an acoustic impedance value that is between that of the ultrasonic elements 120 and tissue of a subject (e.g., organ tissue, bone, vessel tissue, etc.). In some embodiments, a plurality of layers of materials forming the at least one matching layer 140 may have sequentially descending acoustic impedance values with distance away from the plurality of ultrasonic elements 120. The materials of the at least one matching layer 140 may be composed to provide a selected level of acoustic impedance. For example, the at least one matching layer 140 may include one or more of polymers, epoxies, metal particles (e.g., gold, silver, tungsten, etc.), combinations of any of the foregoing, or any other matching layer materials. In some embodiments, the thickness of each of the at least one matching layers 140 is about a quarter of the wavelength of the ultrasound radiation.

Figure 2:
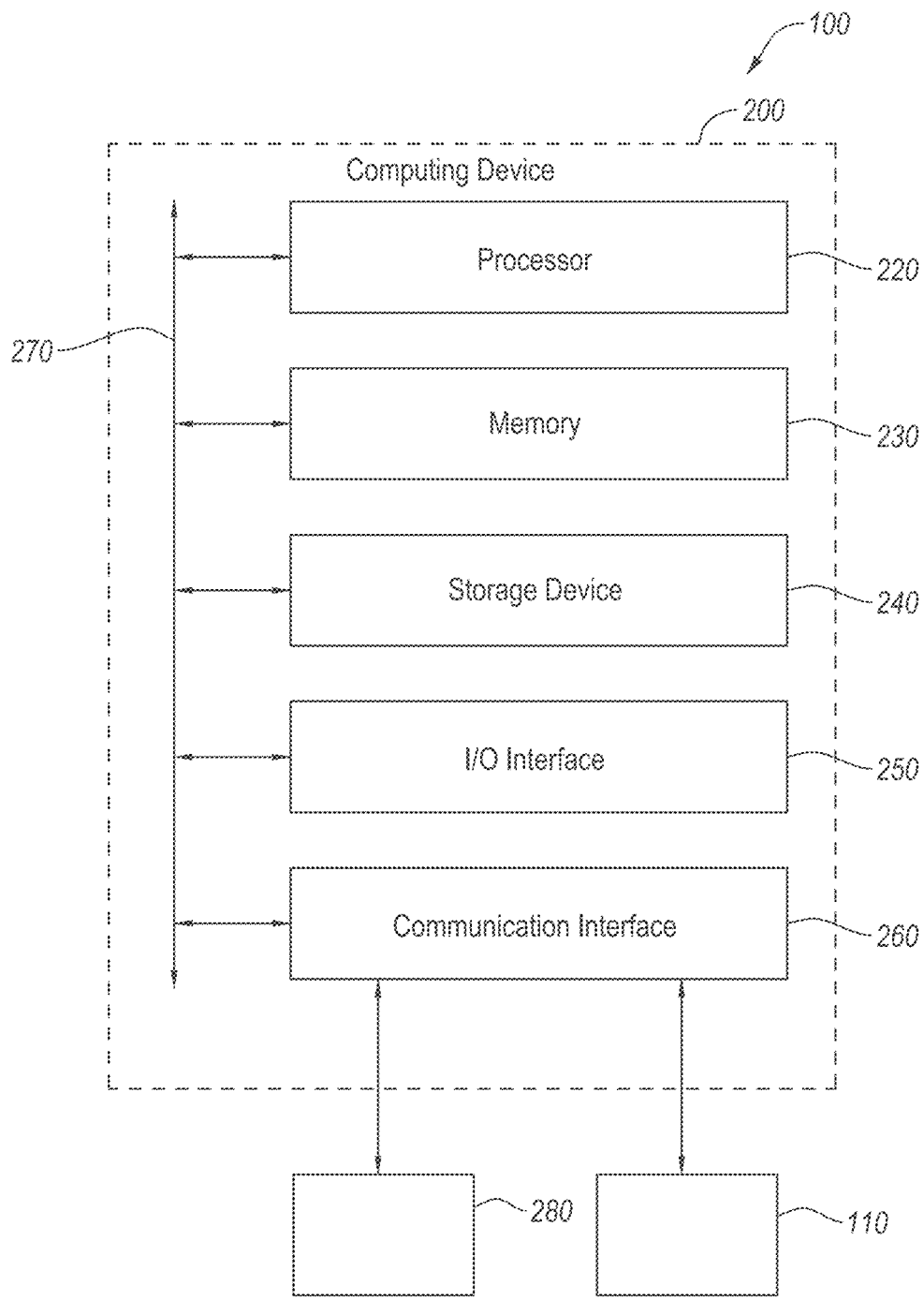
FIG. 2 is a block diagram of the ultrasound imaging system of FIG. 1 with a schematic view of the computing device therein, according to an embodiment.

FIG. 2 is a block diagram of the system 100 with a schematic view of the computing device 200, according to an embodiment. The system 100 includes at least one computing device 200. The at least one computing device 200 is an exemplary computing device that may be configured to perform, direct, or otherwise cause or carry out one or more of the acts described herein. The at least one computing device 200 can include one or more servers, one or more computers (e.g., desk-top computer, lap-top computer), or one or more mobile computing devices (e.g., smartphone, tablet, etc.). The computing device 200 can comprise at least one processor 220, a memory 230, a storage device 240, an I/O interface 250, and a communication interface 260, and a bus 270. In some embodiments, the system 100 may include one or more additional computing devices 280, such as operably coupled thereto over a network connection.

It should be noted that the components illustrated in the computing device 200 of FIG. 2 are not intended to be limiting of the system 100 or computing device 200. Additional or alternative components may be used in other embodiments. Further, in certain some embodiments, the system 100 or the computing device 200 can include fewer components than those shown in FIG. 2. In some embodiments, the at least one computing device 200 may include a plurality of computing devices, a computational network, or cluster of computing devices. Components of computing device 200 shown in FIG. 2 are described in additional detail below.

In some embodiments, the processor(s) 220 includes hardware for executing machine readable instructions (e.g., processing a reasoning graph with selected uniquely identifiable data), such as those making up a computer program. For example, to execute machine readable instructions, the processor(s) 220 may retrieve (or fetch) the instructions from an internal register, an internal cache, the memory 230, or storage device 240 and decode and execute them. In some embodiments, the system 100 includes computing device 200 operably coupled to the ultrasound transducer 110, where the computing device 200 includes memory 230 and the processor 220 operably coupled thereto, wherein the memory 230 includes one or more operational programs stored thereon, and wherein the processor 220 can access and execute the one or more operational programs such as via one or more buses therebetween. In particular embodiments, processor(s) 220 may include one or more internal caches for data (e.g., returned ultrasound radiation values such as intensity; ultrasound echo map(s); operating parameters such as power, frequency, dynamic range, etc.); operational programs containing machine readable and executable instructions (e.g., calculations for signal-to-noise ratios and sharpness ratios, modes of operation such as B-line modes, parameters for emitting and detecting ultrasound radiation, etc.), or addresses. As an example, the processor(s) 220 may include one or more instruction caches, one or more data caches, and one or more translation lookaside buffers (TLBs). Instructions in the instruction caches may be copies of operational programs (e.g. machine readable and executable instructions) in memory 230 or storage 240. In some embodiments, the processor 220 may be configured to (e.g., include operational programming stored thereon or executed thereby) control one or more operational parameters of the system 100 such as a power output of the ultrasound transducer, a number of ultrasonic elements used to emit the ultrasound radiation in the ultrasound transducer, an ultrasound beam form, an ultrasound beam focal depth, frequency, dynamic range, generation of an ultrasound echo map, calculation of a signal-to-noise ratio or sharpness ratio, etc.

In some embodiments, the processor 220 is configured to perform any of the acts disclosed herein such as in any of the methods disclosed herein or cause one or more portions of the computing device 200 or system 100 to perform at least one of the acts disclosed herein. Such configurations can include one or more operational programs that are executable by the at least one processor 220. For example, the processor 220 may be configured to automatically control one or more operational parameters of the ultrasound transducer; automatically determine a signal-to-noise ratio, a sharpness ratio, or combinations thereof; automatically generating an ultrasound echo map; etc. The at least one processor 220 may be configured to produce ultrasound echo maps, such as echo maps having a pleural line and zero or more A-lines, and zero or more B-lines. The at least one processor 220 may be configured to output one or more of the ultrasound echo maps, status of the system 100 or portions thereof, current or available operational parameters or settings of the system (e.g., ultrasound transducer 110), such as causing the I/O interface 250 to communicate any of the above to an entity via the communication interface 260. The at least one processor 220 may be configured to provide a report of any of the operational parameters disclosed herein, ultrasound echo maps, or any other information associated with the system 100; such as causing the I/O interface 250 to communicate any of the foregoing, to an entity via the communication interface 260 (e.g., user interface such as a computer screen, tablet, etc.). The at least one processor 220, memory 230, or storage 240 may include programming to receive input from a user, such as from the communication interface 260 (e.g., user input). For example, the at least one processor 220, memory 230, or storage 240 may include programming to accept user input from the communication interface 260 and change one or more operational parameters of the system 100, output one or more ultrasound echo maps, output current or available operational parameters of the system 100, etc. For example, the at least one processor 220 may cause the I/O interface 250 to communicate any of the foregoing to an entity via the communication interface 260.

The at least one computing device 200 (e.g., a server) may include at least one memory storage medium (e.g., memory 230 and/or storage 240). The computing device 200 may include non-transitory memory 230, which is operably coupled to the processor(s) 220. The memory 230 may be used for storing data, metadata, and programs for execution by the processor(s) 220. The memory 230 may include one or more of volatile and non-volatile memories, such as Random Access Memory (RAM), Read Only Memory (ROM), a solid state disk (SSD), Flash, Phase Change Memory (PCM), or other types of data storage. The memory 230 may be internal or distributed memory.

The computing device 200 may include a storage device 240 having storage for storing data, operational programs (e.g., machine readable and executable instructions), ultrasound echo maps, etc. The storage device 240 may be operably coupled to the at least one processor 220. In some embodiments, the storage device 240 can comprise a non-transitory memory storage medium, such as any of those described above. The storage device 240 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 240 may include removable or non-removable (or fixed) media. Storage device 240 may be internal or external to the computing device 200. In some embodiments, storage device 240 may include non-volatile, solid-state memory. In some embodiments, storage device 240 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some embodiments, one or more portions of the memory 230 and/or storage device 240 (e.g., memory storage medium(s)) may store one or more databases thereon.

In some embodiments, one or more of operational parameters, B-line and non-B-line modes, instructions for calculating signal-to-noise ratio and/or sharpness ratio, calculated signal-to-noise ratio and/or sharpness ratio, ultrasound echo maps, etc., may be stored in a memory storage medium such as one or more of the at least one processor 220 (e.g., internal cache of the processor), memory 230, or the storage device 240 (e.g., non-transitory storage medium such as a compact disk, flash drive, etc.). In some embodiments, the at least one processor 220 may be configured to access (e.g., via bus 270) the memory storage medium(s) such as one or more of the memory 230 or the storage device 240 and execute the operational programs (e.g., machine readable and executable instructions) stored therein, such as accessing and executing any of the methods disclosed herein. For example, the at least one processor 220 may receive and store input from a user, returned ultrasound radiation, ultrasound echo maps, operational parameters for the ultrasound transducer 100, selected modes of operation, as a plurality of data points in the memory storage medium(s).

The computing device 200 also includes one or more input or output (I/O) devices/interfaces 250, which are provided to allow a user to provide input to, receive output from, and otherwise transfer data to and from the computing device 200. These I/O devices/interfaces 250 may include a mouse, keypad or a keyboard, a touch screen, camera, optical scanner, network interface, web-based access, modem, other known I/O devices or a combination of such I/O devices/interfaces 250. The touch screen may be activated with a stylus or a finger.

The I/O devices/interfaces 250 may include one or more devices for presenting output to a user, including, but not limited to, a graphics engine, a display (e.g., a display screen or monitor), one or more output drivers (e.g., display drivers), one or more audio speakers, and one or more audio drivers. In certain some embodiments, devices/interfaces 250 are configured to provide graphical data (e.g., operational parameters, operational modes, ultrasound echo maps, and/or textual explanations) to a display (e.g., computer screen) for presentation to a user. The graphical data may be representative of one or more graphical user interfaces and/or any other graphical content as may serve a particular implementation. The I/O devices/interfaces 250 may include user input device operably coupled to, or forming a portion thereof, the computing device 200 and may provide input (e.g., selections of operating parameters) to the computing device 200 for controlling one or more of the plurality of parameters of the ultrasound transducer. In some embodiments, the user input device may include an actuator (e.g., button, file path, toggle, switch, etc.) for at least one B-line mode and at least one non-B-line mode (e.g. standard operating conditions). For example, the at least one B-line mode may cause the ultrasound transducer to emit ultrasound radiation at a frequency below about 15 MHz and to provide an ultrasound echo map having a B-line that includes a signal-to-noise ratio of at least 2. In some embodiments, the at least one B-line mode may cause the ultrasound transducer to emit ultrasound radiation having one or more parameters, or combinations thereof, that are not suitable for providing typical ultrasound echo maps (e.g., parameters that would provide poor B-line artifact resolution in an ultrasound echo map) such as pleural-line structure-focused echo maps. In some embodiments, the at least one B-line mode may include machine readable and executable instructions of the one or more operational programs for automatically controlling a plurality of parameters of the ultrasound transducer for causing the ultrasound transducer to emit ultrasound radiation at a frequency below about 15 MHz and to provide an ultrasound echo map having a B-line that includes a signal-to-noise ratio of at least 2, responsive to actuating the at least one B-line mode.

The computing device 200 can further include a communication interface 260. The communication interface 260 can include hardware, software, or both. The communication interface 260 can provide one or more interfaces for communication (such as, for example, packet-based communication) between the computing device 200 and the ultrasound transducer 110, one or more additional computing devices 280, or one or more networks. For example, communication interface 260 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 260 may be used. For example, the computing device 200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of system 100 or computing device 200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof. Computing device 200 may include any suitable communication interface 260 for any of these networks, where appropriate.

The computing device 200 may include a bus 270. The bus 270 can include hardware, software, or both that couples components of computing device 200 to each other. For example, bus 270 may include an Accelerated Graphics Port (AGP) or other graphics bus, an Enhanced Industry Standard Architecture (EISA) bus, a front-side bus (FSB), a HYPER-TRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

It should be appreciated that any of the acts described herein, such as in any method disclosed herein, may be performed by and/or at the computing device 200. Additionally or alternatively, one or more of the acts described herein may be performed by or at another computing device such as an additional computing device operably coupled to the system 200. For example, some of the acts may be performed by or on a personal computing device of the user (e.g., additional computing device 280), such as a personal computer, smart phone, etc., (e.g., receiving electronic messages), while one or more of the acts may be performed by another computing device (e.g., additional computing device 280), such as a server, that may be operably connected to the computing device 200 of the user (e.g., determination of an insight may be performed by a server that is connected to the computing device of the user via the Internet). Accordingly, one or more elements of system 100 can be remotely distributed from one another (e.g., wirelessly connected) and/or one or more elements of the system 100 can be collocated. For example, selecting an operational program or operational parameter may be performed via the additional computing device 280, communicated to the computing device 200, and applied by the computing device 200 and the ultrasound transducer 100.

In some embodiments, the at least computing device 200 (e.g., controller 220, memory 230) may include one or more operational programs therein configured for controlling/causing a selected power output of the ultrasound transducer, a selected number of ultrasonic elements used to emit the ultrasound radiation in the ultrasound transducer, a selected number of ultrasonic elements used to receive the returned ultrasound radiation, a selected ultrasound beam form, a selected ultrasound beam focal depth, a selected ultrasound frequency, a selected dynamic range, etc.

The computing device 200 may store one or more operational programs thereon. For example, the computing device 200 may include one or more operational programs having machine readable and executable instructions for operating the system 100 to provide high resolution of B-lines in ultrasound echo maps. The machine readable and executable instructions for operating the system 100 to provide high resolution of B-lines in ultrasound echo maps may include machine readable and executable instructions for controlling one or more (e.g., plurality of) operational parameters of the system 100 such as a power output of the ultrasound transducer, a number of ultrasonic elements used to emit the ultrasound radiation in the ultrasound transducer, an ultrasound beam form, an ultrasound beam focal depth, frequency, dynamic range, generation of an ultrasound echo map (e.g., ultrasound images or sonograms), calculation of a signal-to-noise ratio or sharpness ratio, etc. The machine readable and executable instructions for operating the system 100 to provide high resolution (e.g., sensitivity to B-lines) of B-line artefacts in ultrasound echo maps may include machine readable and executable instructions for determining a signal-to-noise ratio, a sharpness ratio, or a combination of a maximized signal-to-noise ratio and sharpness ratio. The machine readable and executable instructions for operating the system 100 to provide high resolution of B-lines in ultrasound echo maps may include machine readable and executable instructions for generating an ultrasound echo map having high resolution of the B-line therein.

Figure 3:
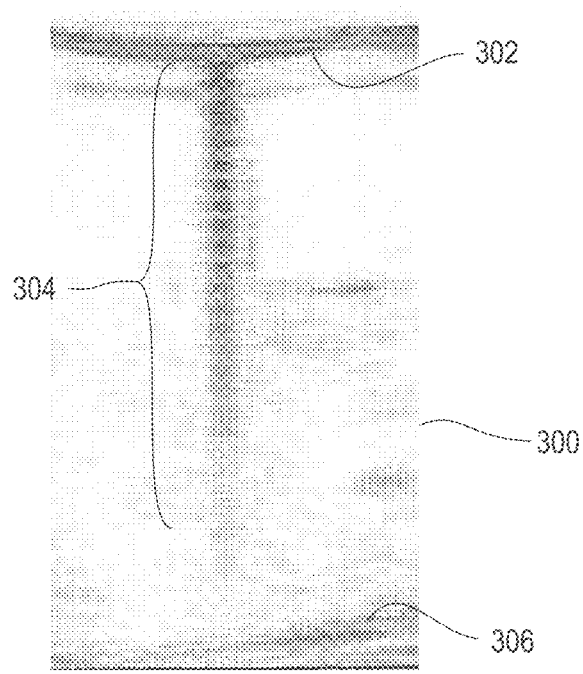
FIG. 3 is a schematic illustration of an ultrasound echo map, according to an embodiment.

Typical ultrasound echo maps of bodies (e.g. body regions/structures), such as a lung, may include a pleural line, A-lines, and B-lines. The pleural line and A-lines are substantially horizontally oriented features on ultrasound echo maps and B-lines are typically vertically oriented (e.g., comet-tail) features, which appear as vertical columns in ultrasound echo maps. FIG. 3 is a schematic illustration of an ultrasound echo map 300, according to an embodiment. The ultrasound echo map 300 may be arranged as an ultrasound image or sonogram. The ultrasound echo map 300 may include a pleural-line 302, which may be a linear structure in the echo map representing an echo boundary of a body structure. The pleural line 302 may be substantially horizontally oriented on the ultrasound echo map, such as linear when using a linear array or may be arcuate when using a curvilinear array. The pleural line 302 may be indicative of a boundary of a body structure, such as an organ, a tissue, etc. For example, the pleural line 302 may indicate a lung, a stomach having gas therein, any other body tissue having a tissue/gas boundary, a wall of any of the foregoing, or any other body structure. In some embodiments, the laterally extending echo boundary may be a pleural line 302 of the lung. The ultrasound echo map 300 may include B-line 304, which may be substantially orthogonal to the pleural line structure. For example, the B-line may extend substantially orthogonally from a laterally extending echo boundary (e.g., pleural line) to a maximum depth of the ultrasound echo map 300. In some embodiments, at least one of the one or more B-lines in an ultrasound echo map extend substantially orthogonally from a substantially laterally extending feature (e.g., pleural line/A-line) in the ultrasound echo map representing the returned ultrasound radiation from a body structure to a maximum depth of the ultrasound echo map. In some embodiments, the B-line 304 may be substantially vertically oriented (e.g., column, line, or comet-tail structure).

The B-line 304 may indicate a fluid in the body structure. For example, the B-line 304 may indicate fluid within a body structure such as a lung. The B-line is a result of hyperechoic reverberation as demonstrated by the artefacts extending in a column in the ultrasound echo map. The B-line may be more intense at a laterally (e.g., horizontally) central portion thereof and may decrease in intensity at lateral extents thereof. In some embodiments, the ultrasound echo map 300 may include one or more A-line echoes 306. The one or more A-line echoes 306 may be echoes of the pleural line 302. The one or more A-line echoes 306 may be spaced from the pleural line 302 by a distance. The distance between the pleural line 302 and the A-line echoes 306, or a discrete portion thereof, may be a vertical range of the B-line 304. In some embodiments, the surface of the skin of a subject or ultrasound transducer may be visible in the ultrasound echo map 300.

For example, the B-line may 304 extend from a first pleural line 302 structure to an echo 306 of the pleural line structure 302 in the ultrasound echo map 300 and the vertical range includes a discrete vertical distance between the first pleural line 302 structure and the echo 306 of the pleural line 302 in the ultrasound echo map 300. In some embodiments, the ultrasound echo map 300 may include various degrees of background noise (not shown), which may appear as a lesser shade of the B-line and/or A-line.

Traditional ultrasound parameters—ultrasound parameters that are useful for detecting tissues or other structures—are not particularly useful for detecting fluid in lungs (e.g., generating high resolution B-line ultrasound echo maps). Accordingly, the systems and methods herein utilize (e.g., provide) selected operational parameters to provide high resolution B-line ultrasound echo maps (e.g., ultrasound echo maps providing high contrast between B-lines and pleural lines and/or background noise such that the echo map has any of the signal-to-noise and/or sharpness ratios disclosed herein). For example, the systems and methods herein may employ one or more operational programs including machine readable and executable instructions for automatically controlling a plurality of parameters of the ultrasound transducer. The plurality of parameters may include one or more of a power output of the ultrasound transducer, a number of ultrasonic elements used to emit the ultrasound radiation in the ultrasound transducer, an ultrasound beam form, an ultrasound beam focal depth, an emitted ultrasound radiation frequency, or a dynamic range.

In some embodiments, the one or more operational programs may include machine readable and executable instructions for automatically controlling power parameters, such as for causing the ultrasound transducer to output the ultrasound radiation at a power output value (e.g., ultrasound radiation/energy intensity) that is less than a maximum power output value of the ultrasound transducer 110, such as less than about half, less than about one third, less than about one quarter, less than about one tenth of the maximum power output value of the ultrasound transducer 110, or a range between any combination of the preceding values. In some embodiments, the machine readable and executable instructions of the one or more operational programs are for automatically providing a power output value for the plurality of ultrasonic elements in the ultrasound transducer for causing the plurality of ultrasonic elements to operate at less than a maximum power output of the plurality of ultrasonic elements. For example, the machine readable and executable instructions of the one or more operational programs may cause the plurality of ultrasonic elements to operate at less than about half of the maximum power output of the plurality of ultrasonic elements, less than about one third, less than one quarter, or less than about one tenth of the maximum power output of the plurality of ultrasonic elements.

In some embodiments, the one or more operational programs may include machine readable and executable instructions for automatically controlling a plurality of parameters of the system 100 (e.g., ultrasound transducer), such as for causing (e.g., effective to cause) the ultrasound transducer to output the ultrasound radiation at a frequency below about 15 MHz, such as below about 13 MHz, below about 12 MHz, below about 10 MHz, below about 9 MHz, below about 8.5 MHz, below about 8.5 MHz, below about 8 MHz, below about 7.5 MHz, below about 7 MHz, below about 6.5 MHz, below about 6 MHz, below about 5.5 MHz, below about 5.0 MHz, below about 4.5 MHz, below about 4 MHz, below about 3.5 MHz, below about 3 MHz, about 3 MHz to about 10 MHz, about 5 MHz to about 12 MHz, about 3 MHz to about 8 MHz, or a range including endpoints of any combination of the preceding frequency values. In some embodiments, the frequency of the emitted ultrasonic radiation may be greater than 15 MHz (e.g., less than about 20 MHz). In some embodiments, the returned ultrasound radiation may be a harmonic of the emitted ultrasound radiation. Other embodiments may operate in non-harmonic mode, i.e., the returned ultrasound radiation is the same frequency as the emitted ultrasound radiation. Accordingly, the operating instructions may include machine readable and executable instructions for setting the ultrasonic elements 120 to receive returned ultrasound radiation, either non-harmonically or harmonically.

In some embodiments, the one or more operational programs may include machine readable and executable instructions for automatically controlling how many ultrasonic elements are used to emit and receive the ultrasound radiation, such as for causing (e.g., effective to restrict) the ultrasound transducer to use less than the total number of ultrasonic elements 120, such as less than about two thirds, less than about half, less than about one third, less than about one quarter, less than about one tenth of the total number of ultrasonic elements 120, or a range between any combination of the preceding values. For example, the one or more operational programs may include machine readable and executable instructions for restricting a number of the plurality of ultrasonic elements from emitting ultrasound radiation such that between about 4 and about 13 ultrasonic elements 120 emit ultrasound radiation and/or receive (e.g., detect) returned ultrasound radiation.

In some embodiments, the one or more operational programs may include machine readable and executable instructions for automatically controlling a focal depth of the ultrasound transducer 110 or plurality of ultrasonic elements 120 therein. For example, one or more operational programs may include machine readable and executable instructions for the plurality of ultrasonic elements 120 for causing the ultrasound transducer 110 to have a focal point at a boundary of or above an interrogation site (e.g., target site of a sonogram such as an organ wall, internal organ structure, tissue, etc.), such as at least about 0 mm above the interrogation site, at least about 1 mm above the interrogation site, about 2 mm above the interrogation site, about 3 mm above the interrogation site, about 4 mm above the interrogation site, about 5 mm above the interrogation site, about 10 mm above the interrogation site, about 15 mm above the interrogation site, or a range including endpoints having any of the preceding values (e.g., about 0 mm to about 10 mm or about 5 mm to about 10 mm above an interrogation site). For example, an interrogation site may include a lung for determining the presence of fluid in the lung, and the machine readable and executable instructions may focus the ultrasound radiation at a point about 0 mm to about 10 mm above a lung wall or an internal point within the lung. Such a spatial relationship (e.g., offset) in the distance between the interrogation site and the focal point of the ultrasound radiation provides high resolution of (e.g., high sensitivity and/or contrast resulting in signal-to-noise and/or sharpness ratios as disclosed herein) B-line artefacts in the resulting ultrasound echo maps. For example, rather than focusing the ultrasound radiation in the body structure, an operational program may direct the ultrasound transducer to focus the emitted ultrasound radiation at a boundary of the body structure or thereabove. Such a focal point may provide high resolution B-line information of fluid within the body structure, beneath the focal point. In some embodiments, the one or more operational programs may include machine readable and executable instructions for the plurality of ultrasonic elements 120 for causing the ultrasound transducer 110 to have a focal point at a boundary of or below an interrogation site such as at least about 1 mm below an interrogation site.

In some embodiments, the one or more operational programs may include machine readable and executable instructions for automatically controlling the plurality of ultrasonic elements for causing the ultrasound transducer to emit ultrasound radiation having a focused beam form in comparison to a single plane wave, multi-angle plane wave, weakly focused overlapping beam, or spatial compounding.

In some embodiments, the one or more operational programs may include machine readable and executable instructions for automatically controlling a plurality of parameters of the system 100 (e.g., ultrasound transducer) such as for causing (e.g., effective to cause) the ultrasound transducer to output the ultrasound radiation for providing an ultrasound echo map having a B-line that includes a signal-to-noise ratio of at least 2, such as more than about 5, more than about 8, more than about 10, more than about 15, more than about 20, more than about 25, more than about 30, more than about 40, or ranges including any of the foregoing values as endpoints. The signal-to-noise ratios and ranges thereof herein may be used in combination with any other parameters or ultrasound radiation properties disclosed herein. For example, the inventors have found that using a plurality of settings not used for searching for pleural lines, such as a frequency below about 15 MHz or even less as disclosed herein, can result in a signal-to-noise ratio of more than about 2 (e.g., more than about 8, more than about 10, more than about 15, and more than about 25 in some cases).

A signal-to-noise ratio may be defined as a ratio of a sum of intensities of the ultrasound echo map in a discrete B-line region laterally centered on a B-line of the one or more B-lines versus a sum of intensities of the ultrasound echo map outside of and on both sides of the B-line. For example, the signal-to-noise ratio may be a sum of intensities of the ultrasound echo map in a discrete region laterally centered on and bound within a lateral portion of a B-line of the one or more B-lines and within a longitudinal range encompassing the B-line versus a sum of intensities of the ultrasound echo map outside of and adjacent to both sides of the B-line to a lateral distance from both sides of the B-line within the longitudinal range encompassing the B-line. In some embodiments, the intensities may be intensities of returned ultrasound radiation, returned radio frequency radiation intensity, or an intensity of a pixel generated on a display and representing any of the preceding. Such embodiments may automatically compare the most intense returned ultrasound radiation or signal thereof in the B-line to a background noise level outside of, but adjacent to, the B-line to some selected distance therefrom. In some embodiments, the one or more operational programs may include machine readable and executable instructions for automatically determining the signal-to-noise ratio.

In some embodiments, the machine readable and executable instructions of the one or more operational programs may be for automatically controlling a plurality of parameters of the ultrasound transducer for causing (e.g., effective to cause) the ultrasound transducer to emit ultrasound radiation at a frequency (e.g., below about 15 MHz) to provide an ultrasound echo map having a B-line that includes a sharpness ratio greater than about 0.2, such greater than about 0.25, greater than about 0.3, greater than about 0.35, greater than about 0.4, greater than about 0.45, greater than about 0.5, greater than about 0.6, greater than about 0.7, greater than about 0.8, or ranges including endpoints having any of the foregoing values. In some embodiments, the sharpness ratio may include a sum of intensities of the ultrasound echo map in a discrete B-line region versus a sum of intensities of the ultrasound echo map in an entire lateral dimension of the B-line. In some embodiments, the intensities may be intensities of returned ultrasound radiation, returned radio frequency radiation intensity, or an intensity of a pixel generated on a display and representing any of the preceding. Such embodiments may automatically compare the most intense returned ultrasound radiation or signal thereof in the B-line to a remainder of the returned ultrasound radiation or signal thereof in the entire B-line to determine a sharpness of the B-line. In some embodiments, the one or more operational programs may include machine readable and executable instructions for automatically determining the sharpness ratio.

In some embodiments, the machine readable and executable instructions of the one or more operational programs may be for automatically controlling a plurality of parameters of the ultrasound transducer for causing (e.g., effective to cause) the ultrasound transducer to emit ultrasound radiation at a frequency (e.g., below about 15 MHz) to provide an ultrasound echo map having a B-line that includes a combination of a maximized signal-to-noise ratio and a maximized sharpness ratio. A maximized signal-to-noise ratio and/or sharpness ratio may be a maximum possible signal-to-noise ratio or sharpness ratio for a selected set of operational parameters or ranges thereof. The operational parameters for the combination of a maximized signal-to-noise ratio and maximized sharpness ratio may be selectively adjusted or controlled to balance the signal-to-noise ratio and the sharpness ratio to achieve maximum value for the combination of both ratios. Accordingly, the combination of a maximized signal-to-noise ratio and maximized sharpness ratio may not provide the maximum signal-to-noise ratio or maximum sharpness ratio when viewed in isolation from each other, but rather, strike a balance between maximizing both ratios. In some embodiments, the combination of the maximized signal-to-noise ratio and the maximized sharpness ratio may include a signal-to-noise ratio of at least about 2 (e.g., 5 or more, 10 or more, 15 or more, 20 or more, 25 or more etc.) and a sharpness value of greater than about 0.2 (e.g., greater than about 0.25, greater than about 0.3, greater than about 0.4, greater than about 0.5, etc.).

In some embodiments, the machine readable and executable instructions of the one or more operational programs are for automatically determining the signal-to-noise ratio and the sharpness ratio, such as using a machine vision system or signal processor to determine the signal-to-noise ratio and the sharpness ratio. In some embodiments, the machine readable and executable instructions of the one or more operational programs may be for automatically determining the combination of a maximized signal-to-noise ratio and a maximized sharpness ratio. For example, an algorithm may determine a maximum signal-to-noise ratio and maximum sharpness ratio, along with the operational parameters associated therewith. The algorithm may determine a combination of operational parameters which provide a combination of a maximized signal-to-noise ratio and a maximized sharpness ratio (e.g., a combination of operational parameters which provide both a signal-to-noise ratio and sharpness ratio having a maximum value). In some instances, the maximum possible signal-to-noise ratio and/or sharpness ratio may not be used in the combination of a maximized signal-to-noise ratio and a maximized sharpness ratio, because some operational parameters of the maximized sharpness ratio may limit the signal-to-noise ratio and vice versa.

In some embodiments, the one or more operational programs may include machine readable and executable instructions that control and combine any combination of the operational parameters disclosed herein. For example, the machine readable and executable instructions of the one or more operational programs may automatically control a plurality of parameters of the ultrasound transducer for causing one or more of: the ultrasound transducer to emit ultrasound radiation at a frequency of about 3 MHz to about 10 MHz (or any other frequency disclosed herein) to provide an ultrasound echo map having a B-line that includes a combination of a maximized signal-to-noise ratio and a maximized sharpness ratio; a power output value of a plurality of ultrasonic elements to operate at less than about one quarter of a maximum power output of the plurality of ultrasonic elements (or any other power output value disclosed herein); a number of the plurality of ultrasonic elements in the ultrasound transducer from emitting ultrasound radiation such that about 4 to about 13 of the plurality of the ultrasonic elements (or any other number of ultrasonic elements disclosed herein) emit ultrasound radiation; and the ultrasound transducer to emit ultrasound radiation having a dynamic range value that is less than about one third of a maximum dynamic range value of the ultrasound transducer.

A user input device may be operably coupled to the computing device to provide input to the computing device for controlling one or more of the plurality of parameters of the ultrasound transducer. For example, the computing device may include one or more operational programs, such as at least one B-line mode and at least one non-B-line mode, each having machine readable and executable instructions for causing one or more operational parameters to actuate, adjust, maintain, or terminate. A user may select the at least B-line mode at the user input device, such as via an actuator (e.g., button, switch, etc.). The at least one non-B-line mode may be a traditional or standard mode of operation for an ultrasound transducer such as for identifying body structures such as organs, tissues, etc. The at least one B-line mode may include operational parameters that are not desirable for identifying body structures, but provide high resolution of (e.g., high sensitivity to) B-line artefacts in ultrasound echo maps. In some embodiments, the at least one B-line mode may provide operational programs that include machine readable and executable instructions for controlling any of the operational parameters disclosed herein, wherein such operational parameters are specifically selected to provide high resolution of B-line artefacts in ultrasound echo maps. For example, the at least one non-B-line mode may include operational programs providing a power output value for the plurality of ultrasonic elements in the ultrasound transducer and the at least one B-line mode may include operational programs providing a power output value for the plurality of ultrasonic elements that is less than the power output value of the at least one non-B-line mode, such as less than about half of the at least one non-B-line mode, less than about one third, less than about one quarter, or less than about one tenth of the power output value of the at least one non-B-line mode.

The at least one non-B-line mode may include operational programs providing an ultrasound radiation frequency output value for the plurality of ultrasonic elements in the ultrasound transducer and the at least one B-line mode may include operational programs providing a ultrasound radiation frequency output value for the plurality of ultrasonic elements that is less than the ultrasound radiation frequency output value of the at least one non-B-line mode, such as less than about eighty five percent of the at least one non-B-line mode, less than about two thirds (e.g., 66%), less than about half, less than about one third, less than about one quarter, or less than about one tenth of the ultrasound radiation frequency output value of the at least one non-B-line mode.

The at least one non-B-line mode may include operational programs having machine readable and executable instructions for providing an ultrasound radiation from the plurality of ultrasonic elements and the at least one B-line mode may include operational programs having machine readable and executable instructions for providing a ultrasound radiation from less than all of the plurality of ultrasonic elements, such as less than about two thirds of the plurality of ultrasonic elements (e.g., number of ultrasonic elements used in the least one non-B-line mode), less than about one half, less than about one third, less than about one quarter, or less than about one tenth of the plurality of ultrasonic elements. For example, the at least one B-line mode may include machine readable and executable instructions for restricting the number of ultrasonic elements that emit ultrasound radiation (and/or detect returned ultrasound radiation) to between about 4 and about 13 ultrasonic elements. For example, the at least one B-line mode may include machine readable and executable instructions for restricting the number of ultrasonic elements that emit ultrasound radiation to less than all ultrasonic elements while all of the ultrasonic elements may receive the returned ultrasound radiation.

In some embodiments, the at least one B-line mode includes machine readable and executable instructions for the plurality of ultrasonic elements for causing the ultrasound transducer to have a focal point at or above an interrogation site, such as at an interrogation site or least about 1 mm above the interrogation site, about 2 mm above the interrogation site, about 3 mm above the interrogation site, about 4 mm above the interrogation site, about 5 mm above the interrogation site, about 10 mm above the interrogation site, about 15 mm above the interrogation site, or a range including endpoints having any of the preceding values (e.g., about 0 mm to about 10 mm or about 5 mm to about 10 mm above an interrogation site).

In some embodiments, the at least one B-line mode includes machine readable and executable instructions for the plurality of ultrasonic elements for causing the ultrasound transducer to emit ultrasound radiation having a dynamic range value that is less than the at least one non-B-line mode dynamic range value of the ultrasound transducer, such as less than about half, less than about one third, less than about one quarter, less than about one tenth of the dynamic range value of the at least one non-B-line mode.

In some embodiments, the at least one B-line mode includes machine readable and executable instructions for the plurality of ultrasonic elements for causing the ultrasound transducer to emit ultrasound radiation having a focused beam form in comparison to a single plane wave, multi-angle plane wave, weakly focused overlapping beam, or spatial compounding.

The at least one B-line mode may automatically control any combination of operational parameters and values thereof disclosed herein. For example, the at least one non-B-line mode may include operational programs providing a power output value, frequency value, number of ultrasonic elements emitting or receiving ultrasound radiation, etc., for the plurality of ultrasonic elements in the ultrasound transducer, and the at least one B-line mode includes operational programs providing a power output value for the plurality of ultrasonic elements that is less than the power output value of the at least one non-B-line mode, frequency value that is less than the frequency value of the at least one non-B-Line mode, a number of ultrasonic elements that emit or receive ultrasound radiation that is less than those used in a non-B-line mode, etc.

In some embodiments, any combinations of the operational parameters or values thereof of the system 100 may be selectively controlled to provide a high resolution ultrasound echo map (e.g., at any of the signal to noise ratios disclosed herein) such that the presence of a fluid in a body structure (e.g., lung) can be determined. For example, the at least one B-line mode may include machine readable and executable instructions for causing the ultrasound transducer to emit ultrasound radiation at a frequency below about 15 MHz and to provide an ultrasound echo map having one or more B-lines that include a signal-to-noise ratio of at least 2. In some embodiments, the at least one B-line mode may include machine readable and executable instructions for causing the ultrasound transducer to emit ultrasound radiation at a frequency below about 15 MHz and to provide an ultrasound echo map having one or more B-lines that include a signal-to-noise ratio of at least 8. In some embodiments, the at least one B-line mode may include machine readable and executable instructions for causing the ultrasound transducer to emit ultrasound radiation at a frequency below about 10 MHz and to provide an ultrasound echo map having one or more B-lines that include a signal-to-noise ratio of at least 5. In some embodiments, the at least one B-line mode may include machine readable and executable instructions for causing the ultrasound transducer to emit ultrasound radiation at a frequency below about 10 MHz and to provide an ultrasound echo map having one or more B-lines that include a signal-to-noise ratio of at least 8. In some embodiments, the at least one B-line mode may include machine readable and executable instructions for causing the ultrasound transducer to emit ultrasound radiation at a frequency below about 7.5 MHz and to provide an ultrasound echo map having one or more B-lines that include a signal-to-noise ratio of at least 10.

Figure 4:
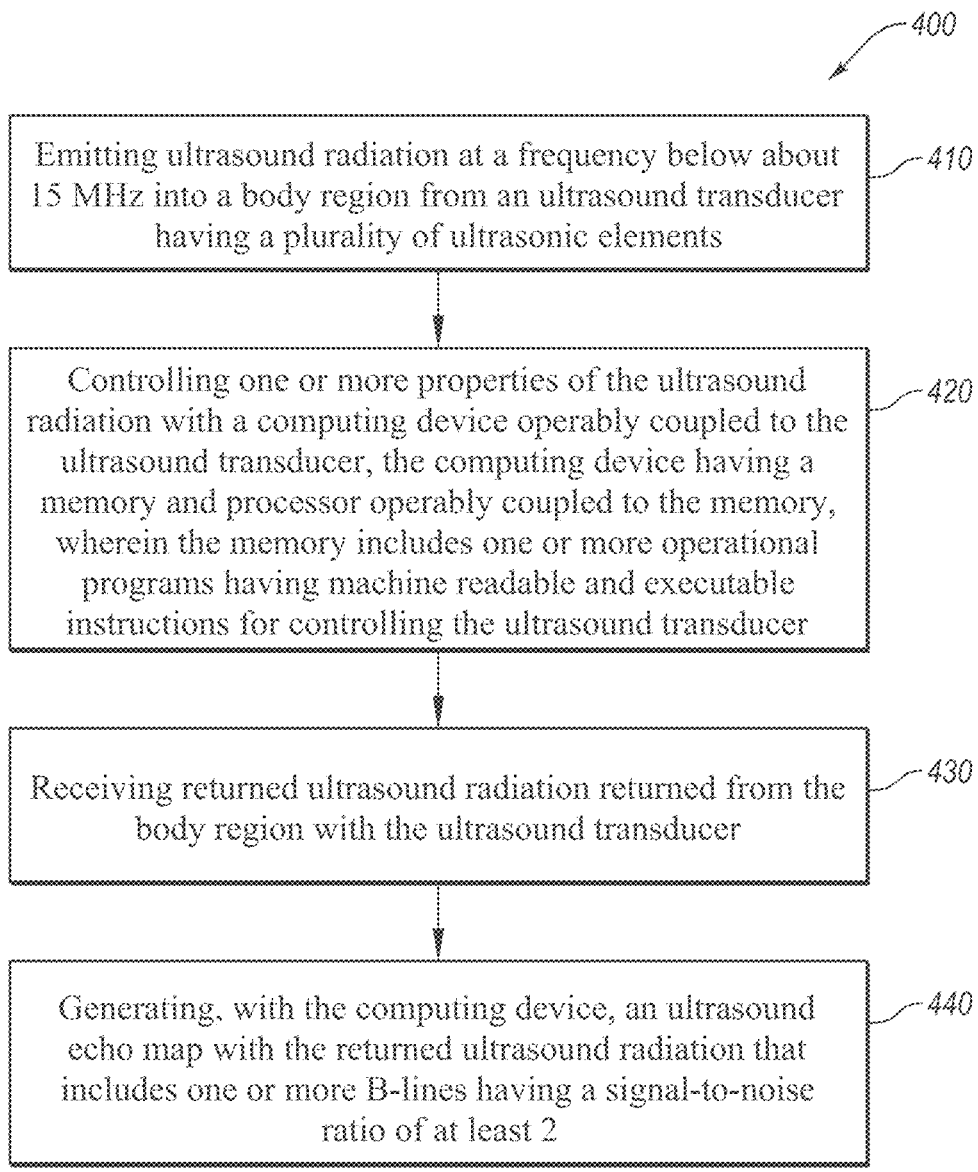
FIG. 4 is a flow chart of a method for determining a presence of fluid in a body, according to an embodiment.

FIG. 4 is a flow chart of a method 400 for determining a presence of fluid in a body, according to an embodiment. The method 400 includes an act 410 of emitting ultrasound radiation at a frequency below about 15 MHz into a body region from an ultrasound transducer having a plurality of ultrasonic elements. The method 400 includes an act 420 of controlling one or more properties of the ultrasound radiation with a computing device operably coupled to the ultrasound transducer, the computing device having a memory and processor operably coupled to the memory, wherein the memory includes one or more operational programs having machine readable and executable instructions for controlling the ultrasound transducer. The method 400 includes an act 430 of receiving returned ultrasound radiation returned from the body region with the ultrasound transducer. The method 400 includes an act 440 of generating, with the computing device, an ultrasound echo map with the returned ultrasound radiation that includes a B-line having a signal-to-noise ratio of at least 2.

The act 410 of emitting ultrasound radiation at a frequency below about 15 MHz into a body region from an ultrasound transducer having a plurality of ultrasonic elements may include using any of the ultrasound systems disclosed herein. The act 410 of emitting ultrasound radiation at a frequency below about 15 MHz into a body region from an ultrasound transducer having a plurality of ultrasonic elements may include emitting ultrasound radiation into, onto, or near a selected body part, structure, or region of a subject. For example, act 410 of emitting ultrasound radiation at a frequency below about 15 MHz into a body region from an ultrasound transducer having a plurality of ultrasonic elements may include emitting ultrasound radiation into a lung of the subject. In some embodiments, emitting ultrasound radiation at a frequency below about 15 MHz into a body region from an ultrasound transducer having a plurality of ultrasonic elements may include emitting ultrasound radiation at a frequency below about below about 13 MHz, below about 12 MHz, below about 10 MHz, below about 9 MHz, below about 8.5 MHz, below about 8 MHz, below about 7.5 MHz, below about 7 MHz, below about 6.5 MHz, below about 6 MHz, below about 5.5 MHz, below about 5.0 MHz, below about 4.5 MHz, below about 4 MHz, below about 3.5 MHz, below about 3 MHz, or a range including endpoints having any combination of the preceding values (e.g., about 3 to about 10 MHz or about 4 MHz to about 8.5 MHz).

In some embodiments, the act 410 of emitting ultrasound radiation at a frequency below about 15 MHz into a body region from an ultrasound transducer may include emitting or causing the plurality of ultrasonic elements to emit ultrasound radiation at less than a maximum power output (e.g., ultrasound radiation intensity) of the plurality of ultrasonic elements. For example, emitting or causing the plurality of ultrasonic elements to emit ultrasound radiation at less than a maximum power output include emitting or causing the plurality of ultrasonic elements to operate at less than about two thirds of the maximum power output of the plurality of ultrasonic elements, less than about one half, less than about one third, less than one quarter, or less than about one tenth of the maximum power output of the plurality of ultrasonic elements.

In some embodiments, the act 410 of emitting ultrasound radiation at a frequency below about 15 MHz into a body region from an ultrasound transducer may include emitting ultrasound radiation from fewer than all of the ultrasonic elements, such as less than about two thirds, less than about half, less than about one third, less than about one quarter, less than about one tenth of the total number of ultrasonic elements, or a range between any combination of the preceding values. For example, emitting ultrasound radiation at a frequency below about 15 MHz into a body region from an ultrasound transducer may include emitting ultrasound radiation from between about 4 and about 13 ultrasonic elements and/or receiving (e.g., detecting) returned ultrasound radiation from fewer than all of the plurality of ultrasound elements, such as any of the amounts listed above.

In some embodiments, the act 410 of emitting ultrasound radiation at a frequency below about 15 MHz into a body region from an ultrasound transducer may include emitting ultrasound radiation to a focal point above an interrogation site in the body region, such as at least at or about 1 mm above the interrogation site, about 2 mm above the interrogation site, about 3 mm above the interrogation site, about 4 mm above the interrogation site, about 5 mm above the interrogation site, about 10 mm above the interrogation site, about 15 mm above the interrogation site, or a range including end points having any of the preceding values (e.g., about 0 mm to about 10 mm above an interrogation site).

In some embodiments, the act 410 of emitting ultrasound radiation at a frequency below about 15 MHz into a body region from an ultrasound transducer may include emitting ultrasound radiation having a focused beam form in comparison to a single plane wave, multi-angle plane wave, weakly focused overlapping beam, or spatial compounding.

The act 410 of emitting ultrasound radiation at a frequency below about 15 MHz into a body region from an ultrasound transducer having a plurality of ultrasonic elements may include using combinations of any of the operational parameters disclosed herein.

In some embodiments, the act 420 of controlling one or more properties of the ultrasound radiation with a computing device operably coupled to the ultrasound transducer, the computing device having a memory and processor operably coupled to the memory, wherein the memory includes one or more operational programs having machine readable and executable instructions for controlling the ultrasound transducer. The computing device may include the computing device 200 (FIG. 2) or one or more components therein. In some embodiments, controlling one or more properties of the ultrasound radiation with a computing device operably coupled to the ultrasound transducer may include controlling one or more of a power output of the ultrasound transducer, a number of ultrasonic elements used to emit the ultrasound radiation in the ultrasound transducer, a number of ultrasonic elements used to receive the ultrasound radiation, an ultrasound beam form, an ultrasound beam focal depth, a frequency of the ultrasound radiation, a dynamic range of the ultrasound radiation, etc.

In some embodiments, the computing device includes a user input operably coupled thereto (e.g., as a component of the computing device), wherein the user input can accept input from a user. In some embodiments, controlling one or more properties of the ultrasound radiation with a computing device operably coupled to the ultrasound transducer may include providing input to the computing device for controlling one or more of a plurality of operational parameters of the ultrasound transducer. Providing input may include selecting an operational program or one or more operational parameters or otherwise inputting instructions at a user input (e.g., user interface), such as using a keyboard, touch screen, switch, or any other selection means. For example, controlling one or more properties of the ultrasound radiation with a computing device operably coupled to the ultrasound transducer may include controlling one or more of a power output of the ultrasound transducer, a number of ultrasonic elements used to emit the ultrasound radiation in the ultrasound transducer, a number of ultrasonic elements used to receive the returned ultrasound radiation, an ultrasound beam form, an ultrasound beam focal depth, a frequency of the ultrasound radiation, or a dynamic range of the ultrasound radiation, by selecting, at the user input, one of the one or more operational programs.

In some embodiments, controlling one or more properties of the ultrasound radiation with a computing device operably coupled to the ultrasound transducer, may include inputting, at the user input, a power output value for the plurality of ultrasonic elements in the ultrasound transducer for causing the plurality of ultrasonic elements to operate at less than a maximum power output, such as any of the power outputs disclosed herein (e.g., less than half, less than one quarter, less than one tenth, etc., of the maximum power output). In some embodiments, controlling one or more properties of the ultrasound radiation with a computing device operably coupled to the ultrasound transducer may include inputting, at the user input, a number of ultrasonic elements that are used to emit the ultrasound radiation to limit the number of ultrasonic elements that emit ultrasound radiation to a number that is less than all of the ultrasonic elements, such as any number of ultrasonic elements disclosed herein (e.g., less than about two thirds, less than about half, less than about one third, less than about one quarter, less than about one tenth, or about 4 to about 13 ultrasonic elements of the plurality of ultrasonic elements). In some embodiments, controlling one or more properties of the ultrasound radiation with a computing device operably coupled to the ultrasound transducer, may include inputting, at the user input, a frequency value for the plurality of ultrasonic elements in the ultrasound transducer for causing the plurality of ultrasonic elements to emit ultrasound radiation at a frequency below about 15 MHz, such as any of those values for frequencies of ultrasound radiation disclosed herein (e.g., less than about 10 MHz, less than about 7.5 MHz, less than about 6.0 MHz, less than about 5.5 MHz, less than about 5.0 MHz, less than about 4.0 MHz, or less than about 3.0 MHz, or ranges including end points having any combination of the preceding frequencies).

In some embodiments, controlling one or more properties of the ultrasound radiation with a computing device operably coupled to the ultrasound transducer may include controlling the one or more properties of the ultrasound radiation via the machine readable and executable instructions of the one or more operational programs for causing the ultrasound transducer to emit ultrasound radiation to provide an ultrasound echo map having a B-line that includes a combination of a maximized signal-to-noise ratio and a maximized sharpness ratio (as described herein). In some embodiments, controlling one or more properties of the ultrasound radiation with a computing device operably coupled to the ultrasound transducer includes controlling a dynamic range of the ultrasound transducer for emitting ultrasonic radiation having a dynamic range value that is less than a maximum dynamic range value of the ultrasound transducer.

In some embodiments, controlling one or more properties of the ultrasound radiation with a computing device operably coupled to the ultrasound transducer may include controlling any combination of the operational parameters disclosed herein. For example, controlling one or more properties of the ultrasound radiation with a computing device operably coupled to the ultrasound transducer includes controlling one or more of (e.g., each of) the frequency of the ultrasound radiation, a power output value of the plurality of ultrasonic elements to operate at less than a maximum power output, a number of the plurality of ultrasonic elements in the ultrasound transducer to individually emit ultrasound radiation such that less than all of the ultrasonic elements emit ultrasound radiation, a number of the plurality of ultrasonic elements in the ultrasound transducer to individually receive returned ultrasound radiation such that all of or less than all of the ultrasonic elements receive returned ultrasound radiation, or a dynamic range of the ultrasound transducer for emitting ultrasonic radiation having a dynamic range value that is less than a maximum dynamic range value of the ultrasound transducer, including any values for any of the operational parameters disclosed herein. For example, less than all ultrasonic elements may emit ultrasound radiation, while all of the ultrasonic elements may receive the returned ultrasound radiation.

In some embodiments, controlling one or more properties of the ultrasound radiation with a computing device operably coupled to the ultrasound transducer may include selecting (e.g., actuating) a B-line mode operational program from the one or more operational programs. In some embodiments, the B-line mode operational program may include any of the operational parameters disclosed herein, such as any of the operational parameters disclosed herein for B-line mode operational programs disclosed herein. For example, the B-line mode operational program may include machine readable and executable instructions to cause the ultrasound transducer to emit ultrasound radiation at a frequency below about 15 MHz or any other frequency value(s) disclosed herein, emit ultrasound radiation at any power value(s) disclosed herein, emit ultrasound radiation from any number of ultrasonic elements disclosed herein, receive returned ultrasound radiation at any number of ultrasonic elements disclosed herein, provide an ultrasound echo map having a B-line that includes any of the signal-to-noise ratio disclosed herein of at least 2, provide an ultrasound echo map having a B-line that includes any of the sharpness ratios disclosed herein of at least 0.2, or emit ultrasound radiation in any dynamic range value disclosed herein, etc., or combinations of any of the foregoing.

In embodiments, controlling one or more properties of the ultrasound radiation with a computing device operably coupled to the ultrasound transducer, the computing device having a memory and processor operably coupled to the memory, wherein the memory includes one or more operational programs having machine readable and executable instructions for controlling the ultrasound transducer may include executing the one or more operational programs stored on a machine readable medium having the operational programs stored therein. For example, controlling one or more properties of the ultrasound radiation with a computing device operably coupled to the ultrasound transducer may include accessing or transferring the one or more operational programs into computing device from a compact disk, flash drive, floppy disk, or any other machine readable medium. In embodiments, any of the operational parameters, B-line modes, or any other operational directions disclosed herein may be stored on a machine readable medium.

In some embodiments, the act 430 of receiving returned ultrasound radiation returned from the body region with the ultrasound transducer may include receiving returned ultrasound radiation at the ultrasound transducer (e.g., ultrasonic elements). In some embodiments, the act 430 of receiving returned ultrasound radiation returned from the body region with the ultrasound transducer may include receiving returned ultrasound radiation at all of the ultrasonic elements that emitted ultrasound radiation (e.g., all of the ultrasonic elements). In some embodiments, receiving returned ultrasound radiation returned (e.g., reflected or scattered) from the body region with the ultrasound transducer may include receiving returned ultrasound radiation at all of or less than all of the plurality of ultrasonic elements, such as any of the number of ultrasonic elements disclosed herein (e.g., less than half to the ultrasonic elements).

In some embodiments, the act 440 of generating, with the computing device, an ultrasound echo map with the returned ultrasound radiation that includes one or more B-lines having a signal-to-noise ratio of at least 2 may include generating, with the computing device, an ultrasound echo map with the returned ultrasound radiation that includes one or more B-lines having a signal-to-noise ratio of at least 2, at least 5, at least 8, at least 10, at least 12, at least 15, at least 20, at least 25, or at least 30, or ranges including end points having any of the preceding values. In some embodiments, the act 440 of generating, with the computing device, an ultrasound echo map with the returned ultrasound radiation that includes one or more B-lines having a signal-to-noise ratio of at least 2 may include generating an ultrasound echo map on a display (e.g., computer screen), such as on the computing device of the ultrasound system. In some embodiments, generating an ultrasound echo map on a display may include processing the returned ultrasound radiation (e.g., electrical signals from the plurality of ultrasonic elements responsive to returned ultrasonic radiation) to determine a position and intensity of the returned ultrasound radiation for a plurality of returned ultrasound radiation signals effective to form the ultrasound echo map.

The method 400 may include determining if one or more characteristics of the ultrasound echo map indicate that a fluid is present in the lung. For example, determining if one or more characteristics of the ultrasound echo map indicate that a fluid is present in the lung may include determining if a B-line is present in the ultrasound echo map. In some embodiments, determining if a B-line is present in the ultrasound echo map may be automatically carried out, by the computing device, according to an operational program, or can be performed by a technician or medical professional. For example, determining if one or more characteristics of the ultrasound echo map indicate that a fluid is present in the lung may include determining if the ultrasound echo map includes a B-line indicative of fluid in the lung. In some embodiments, determining if a B-line is present in the ultrasound echo map may be automatically carried out, by the computing device, according to an operational program may include utilizing an operational program having machine readable and executable instructions for comparing and contrasting the intensity values of the ultrasound echo map effective to identify a B-line artifact/structure in the ultrasound echo map. Such examples may include determining if a signal-to-noise ratio and/or sharpness ratio is above a selected value.

In some embodiments, methods of using any of the systems disclosed herein may include methods of using the ultrasound radiation systems disclosed herein to emit and detect ultrasound radiation in a body region of a subject, without determining that a fluid is present in the body region. In some embodiments, a method of detecting fluid in a body part may include selecting an operational mode of the ultrasound system, wherein the operational mode includes selected operational parameters for outputting ultrasound echo maps capable of detecting B-line artefacts in high resolution.

Figure 5:
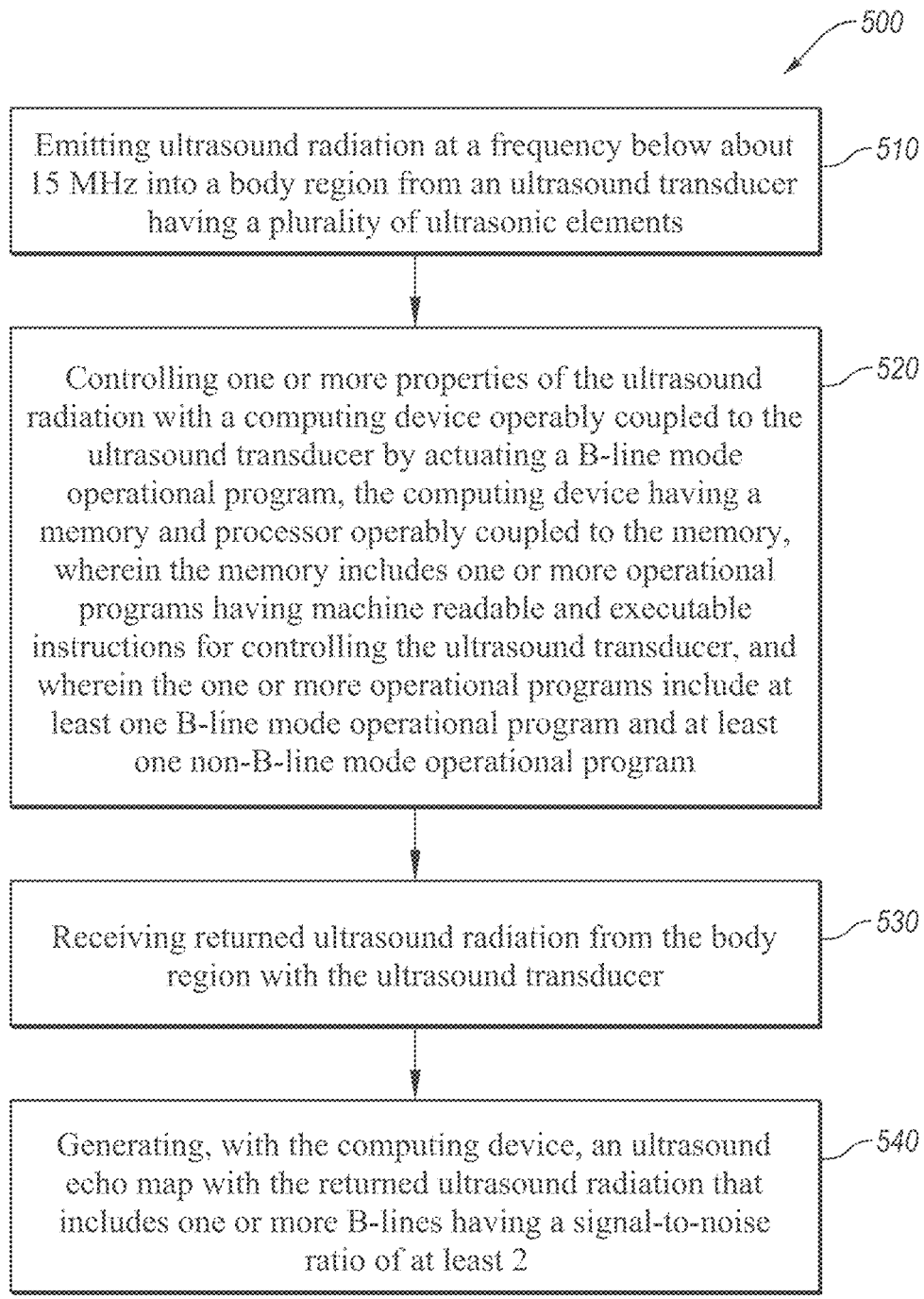
FIG. 5 is a flow chart of a method for determining a presence of fluid in a body, according to an embodiment.

FIG. 5 is a flow chart of a method 500 for determining a presence of fluid in a body, according to an embodiment. The method 500 includes an act 510 of emitting ultrasound radiation at a frequency below about 15 MHz into a body region from an ultrasound transducer having a plurality of ultrasonic elements. The method 500 includes an act 520 of controlling one or more properties of the ultrasound radiation with a computing device operably coupled to the ultrasound transducer by actuating a B-line mode operational program, the computing device having a memory and processor operably coupled to the memory, wherein the memory includes one or more operational programs having machine readable and executable instructions for controlling the ultrasound transducer, and wherein the one or more operational programs include at least one B-line mode operational program and at least one non-B-line mode operational program. The method 500 includes an act 530 of receiving returned ultrasound radiation returned from the body region with the ultrasound transducer. The method 500 includes an act 540 of generating, with the computing device, an ultrasound echo map with the returned ultrasound radiation that includes one or more B-lines having a signal-to-noise ratio of at least 2.

The act 510 of emitting ultrasound radiation at a frequency below about 15 MHz into a body region from an ultrasound transducer having a plurality of ultrasonic elements may be similar or identical to the act 410 disclosed herein, in one or more aspects. For example, emitting ultrasound radiation at a frequency below about 15 MHz into a body region from an ultrasound transducer having a plurality of ultrasonic elements may include one or more of emitting ultrasound radiation with any power output disclosed herein, from any number of ultrasonic elements disclosed herein, any beam form disclosed herein, any ultrasound beam focal depth disclosed herein, any ultrasound radiation frequency disclosed herein, or any dynamic range of the ultrasound radiation disclosed herein. In some embodiments, emitting ultrasound radiation at a frequency below about 15 MHz into a body region from an ultrasound transducer having a plurality of ultrasonic elements may include emitting ultrasound radiation according to one or more operational programs (e.g., a B-line mode or a non-B-line mode).

The act 520 of controlling one or more properties of the ultrasound radiation with a computing device operably coupled to the ultrasound transducer by actuating a B-line mode operational program, the computing device having a memory and processor operably coupled to the memory, wherein the memory includes one or more operational programs having machine readable and executable instructions for controlling the ultrasound transducer, and wherein the one or more operational programs include at least one B-line mode operational program and at least one non-B-line mode operational program. The act 520 of controlling one or more properties of the ultrasound radiation with a computing device operably coupled to the ultrasound transducer by actuating a B-line mode operational program may be similar to the act 420 disclosed above, in one or more aspects. In some embodiments, a non-B-line mode may be configured to interrogate body regions according to standard ultrasound scanning conditions for viewing body structures, such as set-up to scan a uterus, a bladder, a lung, or any other body structure. In some embodiments, the B-line mode may be configured to interrogate body regions (e.g., body regions having an air/tissue interface, such as a lung) according to selected ultrasound scanning conditions for producing and viewing high resolution B-line artifacts, such as set up to scan for fluid in a body region (e.g., a lung). The inventors have discovered that the operational parameters of a B-line mode may differ greatly from operational parameters of non-B-line modes. For example, a reduction in power of ultrasonic radiation may provide a sharper and high contrast B-line (e.g., returned radiation corresponding to a fluid in a body part having an impedance mismatch therein) than a standard or maximum power output from an ultrasound transducer. Limiting the number of ultrasonic elements that emit and/or receive ultrasound radiation may provide a sharper and stronger B-line than a standard or maximum number of ultrasonic elements. As another example, a reduction in frequency of ultrasonic radiation from standard ultrasound probing conditions may provide a sharper and stronger B-line than a standard or maximum frequency output from an ultrasound transducer.

In some embodiments, the machine readable and executable instructions of the one or more operational programs may be for selectively controlling one or more of a power output of the ultrasound transducer or portions thereof (e.g., ultrasonic elements), a number of ultrasonic elements used to emit the ultrasound radiation in the ultrasound transducer, a number of ultrasonic elements used to receive the returned ultrasound radiation, an ultrasound beam form, an ultrasound beam focal depth, an ultrasound radiation frequency, or dynamic range of the ultrasound radiation, in any combination, as disclosed herein.

In embodiments, controlling one or more properties of the ultrasound radiation with a computing device operably coupled to the ultrasound transducer, the computing device having a memory and processor operably coupled to the memory, wherein the memory includes one or more operational programs having machine readable and executable instructions for controlling the ultrasound transducer may include executing one or more operational programs with the computing device from a machine readable medium having the operational programs stored therein. For example, controlling one or more properties of the ultrasound radiation with a computing device operably coupled to the ultrasound transducer may include accessing or transferring the one or more operational programs into the computing device from a compact disk, flash drive, floppy disk, or any other machine readable medium. In embodiments, any of the operational parameters, B-line modes, or any other operational directions disclosed herein may be stored on a machine readable medium.

In some embodiments, the at least one non-B-line mode may include machine readable and executable instructions for the plurality of ultrasonic elements in the ultrasound transducer and the at least one B-line mode may include machine readable and executable instructions for the plurality of ultrasonic elements for only actuating less than all of the ultrasonic elements (e.g., less than about half, less than about a quarter, about 4 to about 13, etc.) of the non-B-line mode.

In some embodiments, the at least one non-B-line mode may include machine readable and executable instructions providing a power output value for the plurality of ultrasonic elements in the ultrasound transducer and the at least one B-line mode includes machine readable and executable instructions providing a power output value for the plurality of ultrasonic elements that is less than the power output value of the at least one non-B-line mode, such as any of the power output values disclosed herein (e.g., less than about half, less than about one third, less than about one quarter, etc.).

In some embodiments, the at least one non-B-line mode may include machine readable and executable instructions providing a first frequency value (e.g. non-B-line mode frequency) for the plurality of ultrasonic elements in the ultrasound transducer, and the at least one B-line mode may include machine readable and executable instructions providing a second frequency value (e.g., B-line mode frequency) for the plurality of ultrasonic elements for causing the second frequency value to be less of the first frequency value of the at least one non-B-line mode. For example, the second frequency (e.g. B-line mode frequency) may be less than about 85% of the first frequency, less than about two thirds, less than about one half, less than about one third, less than about one quarter, or less than about one tenth of first frequency. In some embodiments, the at least one B-line mode may include machine readable and executable instructions providing a second frequency value for the plurality of ultrasonic elements for causing the frequency of the B-line mode to be any of the frequency values disclosed herein, such as less than about 15 MHz, less than about 12 MHz, less than about 10 MHz, less than about 8.5 MHz, less than about 7.5 MHz, less than about 5 MHz, between about 3 MHz and about 10 MHz, between about 4 MHz and about 8.5 MHz, etc.

In some embodiments, the at least one B-line mode may include machine readable and executable instructions for the plurality of ultrasonic elements for causing the ultrasound transducer to have a focal point above an interrogation site (e.g., lung) such as above a proximal surface of an interrogation site (e.g., lung wall). For example, the at least one B-line mode may include machine readable and executable instructions for the plurality of ultrasonic elements for causing the ultrasound transducer to have a focal point at or above the interrogation site by any of the distances disclosed herein such as more than about 1 mm above the interrogation site or about 0 mm to about 10 mm above a proximal surface of an interrogation site.

In some embodiments, the at least one B-line mode may include machine readable and executable instructions for causing the ultrasound transducer to emit ultrasonic radiation having a dynamic range value that is less than a maximum dynamic range value of the ultrasound transducer, such as less than about half of the maximum dynamic range value, less than about one third of the maximum dynamic range value, less than about one quarter of the maximum dynamic range value, or less than about one tenth of the maximum dynamic range value. In some embodiments, the at least one B-line mode may include machine readable and executable instructions for causing the ultrasound transducer to emit ultrasonic radiation having a focused beam form in comparison to a single plane wave, multi-angle plane wave, weakly focused overlapping beam, or spatial compounding wave.

In some embodiments, the at least one B-line mode may include machine readable and executable instructions for causing the ultrasound transducer to emit ultrasonic radiation at a frequency to provide an ultrasound echo map having a B-line that includes a combination of a maximized signal-to-noise ratio and a maximized sharpness ratio. The signal-to-noise ratio and the sharpness ratio and maximized values thereof may be determined as disclosed herein.

As noted above, the machine readable and executable instructions of the operational program for the at least one B-line mode may include machine readable and executable instructions for causing (e.g., effective to cause) one or more of any combination of the operational parameters disclosed herein, such as causing: the ultrasound transducer to emit ultrasound radiation at a frequency of about 3 MHz to about 15 MHz to provide an ultrasound echo map having a B-line that includes a combination of a maximized signal-to-noise ratio and a maximized sharpness ratio; a power output value of a plurality of ultrasonic elements to operate at less than about one quarter of a maximum power output of the plurality of ultrasonic elements; a number of the plurality of ultrasonic elements in the ultrasound transducer from emitting ultrasound radiation such that about 4 to about 13 of the plurality of the ultrasonic elements emit ultrasound radiation; and the ultrasound transducer to emit ultrasonic radiation having a dynamic range value that is less than about one third of a maximum dynamic range value of the ultrasound transducer.

The act 530 of receiving returned ultrasound radiation returned from the body region with the ultrasound transducer may be similar or identical to the act 430 disclosed above, in one or more aspects. For example, receiving returned ultrasound radiation returned from the body region with the ultrasound transducer may include receiving returned ultrasound radiation returned from the body region all or fewer than all of the ultrasonic elements in the ultrasonic transducer.

In some embodiments, the act 530 of receiving returned ultrasound radiation returned from the body region with the ultrasound transducer may include receiving harmonic or non-harmonic ultrasound radiation. In some embodiments, the returned ultrasound radiation may be a harmonic of the emitted ultrasound radiation.

The act 540 of generating, with the computing device, an ultrasound echo map with the returned ultrasound radiation that includes a B-line having a signal-to-noise ratio of at least 2 may be similar or identical to the act 440 disclosed above, in one or more aspects. For example, generating, with the computing device, an ultrasound echo map with the returned ultrasound radiation that includes a B-line having a signal-to-noise ratio of at least 2 may include generating, with the computing device, an ultrasound echo map with the returned ultrasound radiation that includes one or more B-lines having a signal-to-noise ratio of at least 2, at least 5, at least 8, at least 10, at least 12, at least 15, at least 20, at least 25, or at least 30, or ranges including end points having any of the preceding values. In some embodiments, generating, with the computing device, an ultrasound echo map with the returned ultrasound radiation that includes a B-line having a signal-to-noise ratio of at least 2 may include generating, with the computing device, an ultrasound echo map on a user interface device (e.g., computer screen).

Any of the acts, system components, or portions thereof disclosed herein can be used with any of the embodiments disclosed herein.

The systems and methods disclosed herein provide a number of improvements to current systems and methods for determining if a fluid is present in a body part having an impedance mismatch, such as a lung. For example, a reduction in power of ultrasonic radiation may provide a sharper and stronger B-line (e.g., reflected radiation corresponding to a fluid in a body part) than a standard or maximum power output from an ultrasound transducer. Limiting the number of ultrasonic elements that emit and/or receive ultrasound radiation may provide a sharper and stronger B-line than a standard or maximum number of ultrasonic elements. As another example, a reduction in frequency of ultrasonic radiation from standard ultrasound probing conditions may provide a sharper and stronger B-line than a standard or maximum frequency output from an ultrasound transducer.

Working Examples

The following working examples provide further detail in connection with the specific embodiments described above. Experiments were carried out using multiple ultrasound devices in which various operational parameters were selectively altered to provide high resolution B-line artefacts (e.g., B-lines having a signal-to-noise ratio greater than 2, greater than 5, greater than 10, or in some instances greater than 15) in the resulting ultrasound echo maps.

Figure 6:
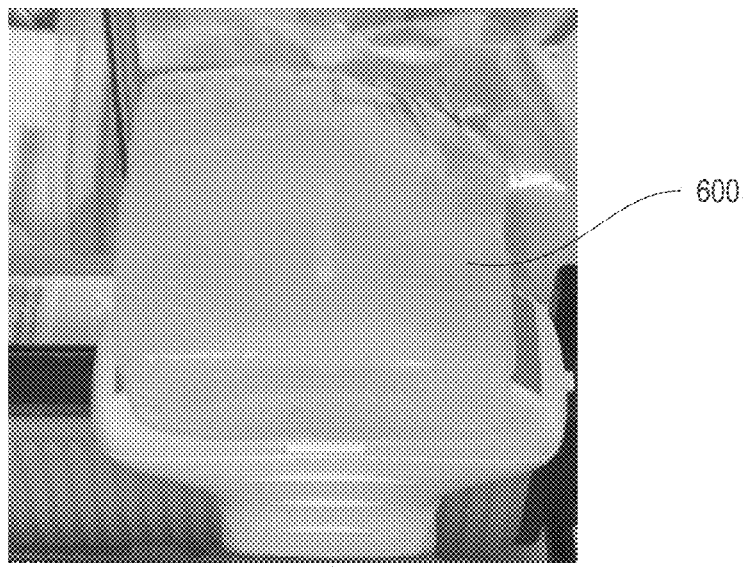
FIG. 6 is a photo of the testing structure containing a phantom lesion.

In working examples 1 and 2, a phantom that mimics human tissue was used to test various ultrasound devices and operational parameters thereof. FIG. 6 is a photo of the testing structure 600 containing a phantom lesion. The testing structure 600 includes 1% agar gel filled bag with a 4% lesion gel forming a phantom lesion therein. The testing structure 600 was subjected to ultrasound probes by various ultrasound devices as disclosed below.

Figure 7A:
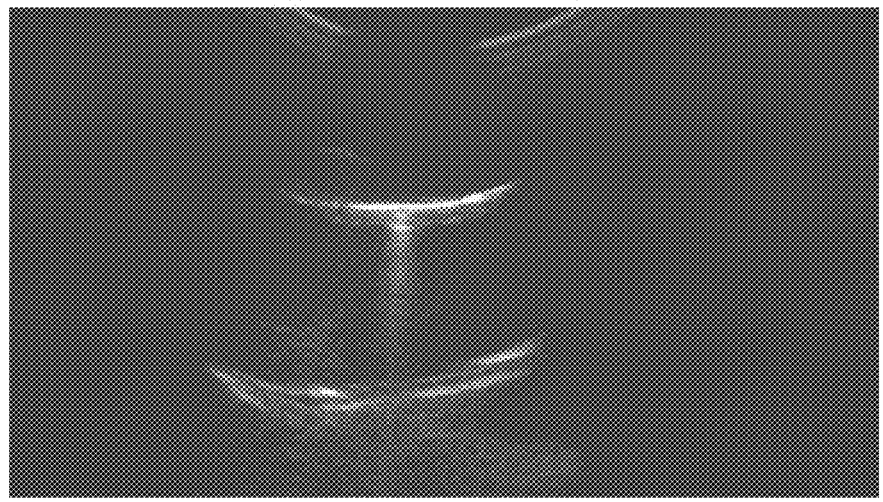
FIGS. 7A-7F are ultrasound echo maps of the testing structure 600 made using various beamforming methods of ultrasound radiation.
Figure 7B:
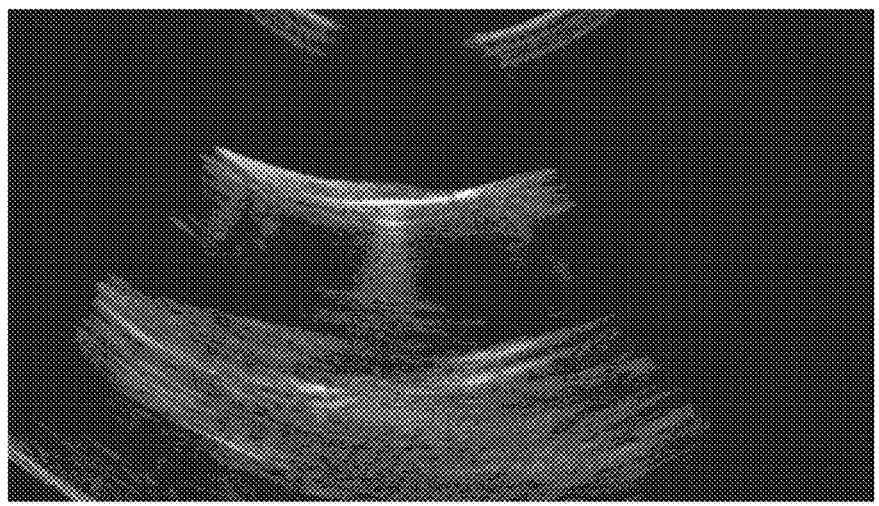
Figure 7C:
Figure 7D:
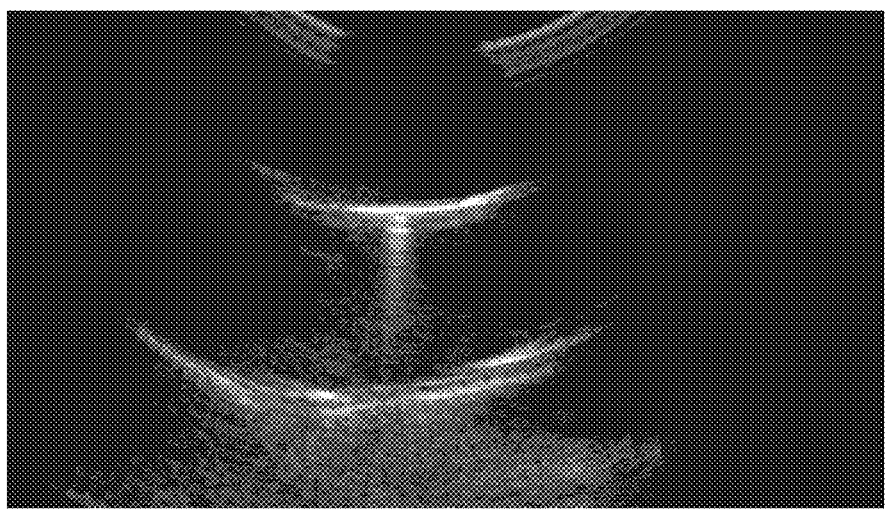
Figure 7E:
Figure 7F:
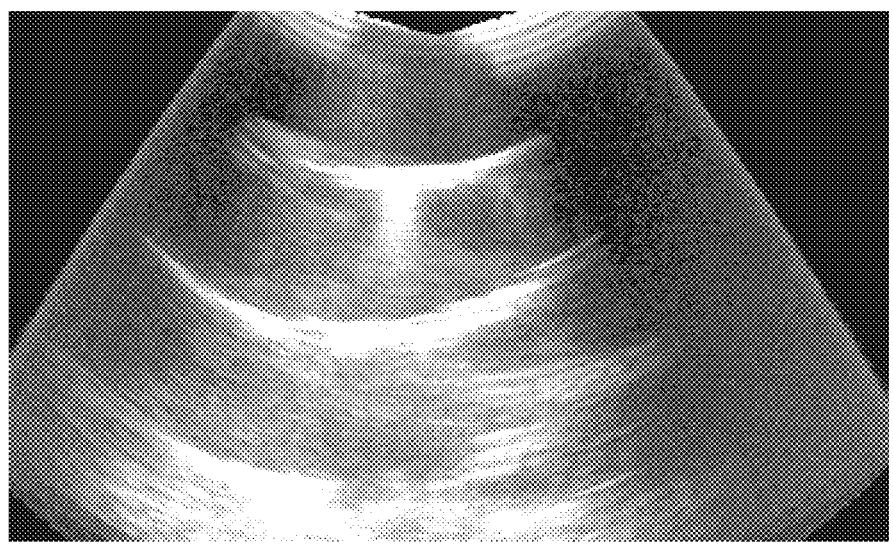

Working example 1 employed a Verasonics Vantage 128™ ultrasound system having a curvilinear array of ultrasonic elements to emit and receive ultrasound radiation having various operational parameters. The Verasonics Vantage 128™ system is commercially available from Verasonics Inc. of Kirkland, Wash., U.S.A. Various numbers of ultrasonic elements (transmitters) were used in a number of probes of the testing structure 600. FIGS. 7A-7F are ultrasound echo maps (e.g. sonograms) of the testing structure 600 made using various beam forming techniques. FIG. 7A is an echo map made using 14 ultrasonic elements to emit ultrasound radiation with 128 ray lines (e.g., a narrow beam width) and 128 ultrasonic elements to receive the returned ultrasonic radiation. FIG. 7B is an echo map made using 128 ultrasonic elements to emit ultrasound radiation and 128 ultrasonic elements in the transducer to receive the returned ultrasonic radiation using a single plane wave. FIG. 7C is an echo map made using 128 ultrasonic elements to emit ultrasound radiation and 128 ultrasonic elements in the transducer to receive the returned ultrasonic radiation using a plane wave at 7 different angles. FIG. 7D is an echo map made using 32 ultrasonic elements to emit ultrasound radiation and 128 ultrasonic elements in the transducer to receive the returned ultrasonic radiation using a weakly focused overlapping beam. FIG. 7E is an echo map made using 32 ultrasonic elements to emit ultrasound radiation and 128 ultrasonic elements in the transducer to receive the returned ultrasonic radiation using a wide beam and harmonic with pulse inversion. FIG. 7F is an echo map made using 70 ultrasonic elements to emit ultrasound radiation and 128 ultrasonic elements in the transducer to receive the returned ultrasonic radiation, with a wide spatially compounding beam and 3 wide beams with 3 steering directions. The signal-to-noise ratio of each of the respective echo maps (calculated as disclosed herein) of FIGS. 7A-7F was 25.2, 8.2 13.0, 19.7, below measurements standards (B-line was not visible to calculate ratio, and 3.2 (from 7A-7F). The sharpness ratio of each of the respective echo maps (calculated as disclosed herein) of FIGS. 7A-7F was 0.35, 0.23, 0.29, 0.36, 0.8, and 0.23 (from FIGS. 7A-7F). FIGS. 7A-7F demonstrate that fewer ultrasound emitters in conjunction with narrowly focused beam forms resulted in relatively high signal-to-noise ratios and relatively high sharpness ratios and relatively high signal-to-noise rations as compared to wide beam forms and higher numbers of ultrasound emitters.

Figure 8A:
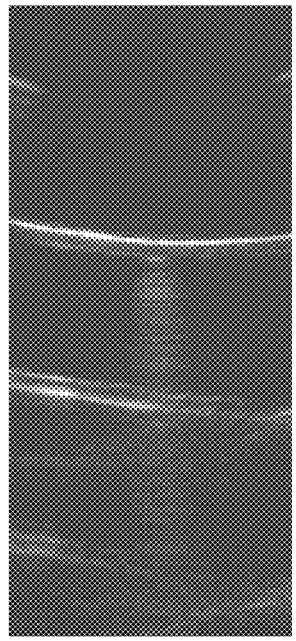
FIGS. 8A-8E are echo maps generated from ultrasound probes of a testing structure each using a different number of ultrasonic elements to emit ultrasound radiation using the same beam forming method.
Figure 8B:
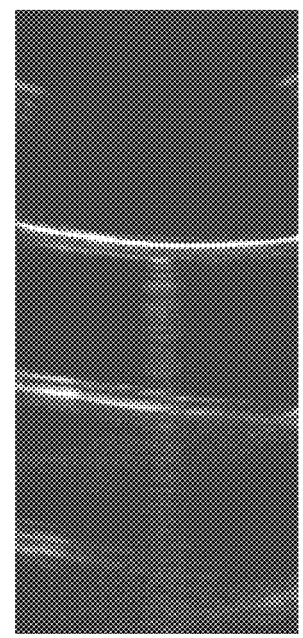
Figure 8C:
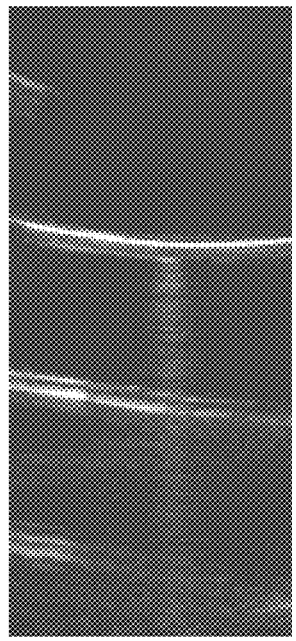
Figure 8D:
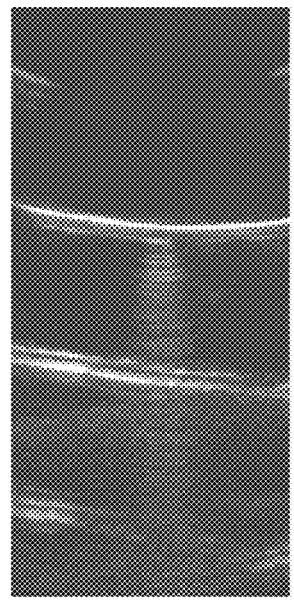
Figure 8E:
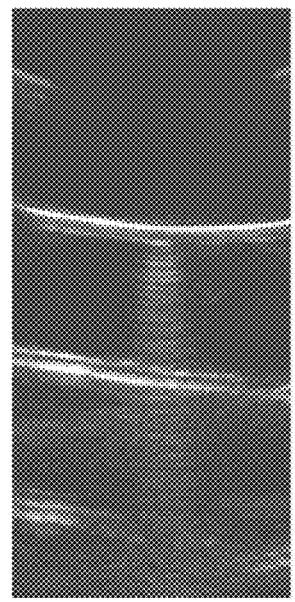
Figure 8F:
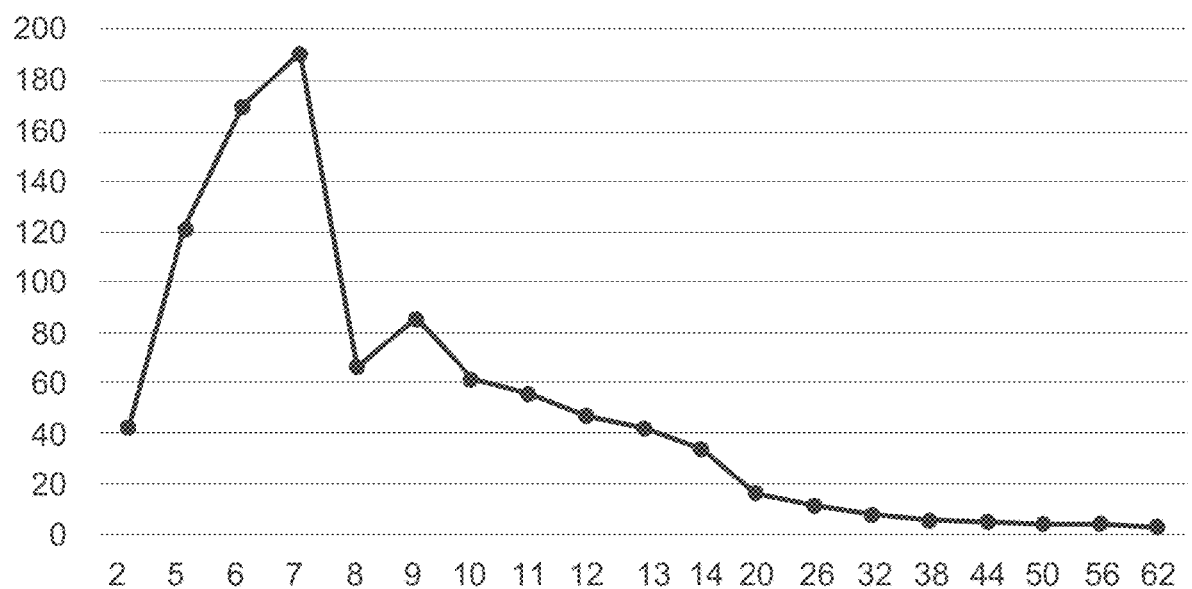
FIG. 8F is a graph of the signal-to-noise ratio versus number of ultrasonic elements versus use to generate the ultrasound echo maps.

FIGS. 8A-8E are echo maps generated from ultrasound probes of a testing structure each using a different number of ultrasonic elements to emit ultrasound radiation using the same beamforming method. The echo maps of FIGS. 8A-8E are generated from ultrasound probes of the testing structure 600 wherein the only difference therebetween was the number of ultrasonic elements used to emit ultrasound radiation from the Vantage 128™ transducer and FIG. 8F is a graph of the number of ultrasonic elements (x-axis) to the signal-to-noise ratio (y-axis) in the ultrasound echo maps corresponding thereto. FIG. 8A is an ultrasound echo map wherein 4 ultrasonic elements were used to emit ultrasound radiation into the phantom. FIG. 8B is an ultrasound echo map wherein 7 ultrasonic elements were used to emit ultrasound radiation into the phantom. FIG. 8C is an ultrasound echo map wherein 10 ultrasonic elements were used to emit ultrasound radiation into the phantom. FIG. 8D is an ultrasound echo map wherein 20 ultrasonic elements were used to emit ultrasound radiation into the phantom. FIG. 8E is an ultrasound echo map wherein 62 ultrasonic elements were used to emit ultrasound radiation into the phantom. As shown in FIG. 8F, the signal-to-noise ratio for the B-line artefacts in the ultrasound echo maps generally dropped as the number of ultrasonic elements increases. This is contrary to standard ultrasound practices for probing A-line artefacts (e.g., organs, etc.)

Figure 9A:
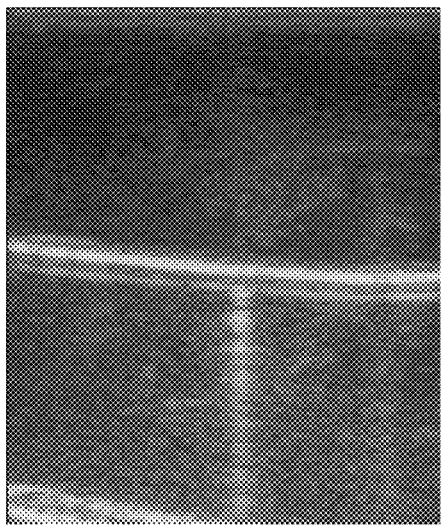
FIGS. 9A-9F are ultrasound echo maps generated from ultrasound probes of a testing structure wherein the frequencies of the ultrasound radiation emitted vary between each figure.
Figure 9B:
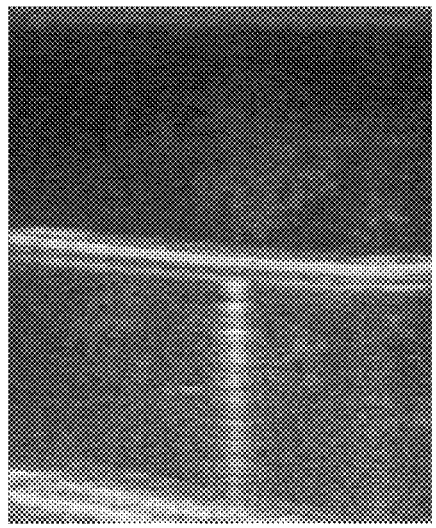
Figure 9C:
Figure 9D:
Figure 9E:
Figure 9F:

Working example 2 employed a Mindray Z5 ultrasound system having a linear array of ultrasonic elements to emit and receive ultrasound radiation having various operational parameters. The Mindray Z5 system is commercially available from Mindray of Shenzhen, China. Various ultrasound radiation frequencies were used in a number of probes of the testing structure 600. FIGS. 9A-9F are ultrasound echo maps generated from ultrasound probes of the testing structure 600 with a focal depth of about 15 mm wherein the frequencies of the ultrasound radiation vary between each figure. FIG. 9A is an echo map generated using ultrasound radiation emitted at 5 MHz. FIG. 9B is an echo map generated using ultrasound radiation emitted at 7.5 MHz. FIG. 9C is an echo map generated using ultrasound radiation emitted at 8.5 MHz. FIG. 9D is an echo map generated using ultrasound radiation emitted at 10 MHz. FIG. 9E is an echo map generated using ultrasound radiation emitted at 8 MHz with harmonic enhancement. FIG. 9F is an echo map generated using ultrasound radiation emitted at 10 MHz with harmonic enhancement. As shown in FIGS. 9A-9D, lower frequencies (5 MHz) that do not include harmonic enhancement provide a higher signal-to-noise ratio than higher frequencies. FIGS. 9A-9D show that increasing the frequency of the ultrasound radiation resulted in increasing noise on the Mindray Z5 ultrasound system.

In embodiments, performing any of the methods disclosed herein can include using a non-transitory computer readable medium including one or more machine readable instructions (e.g., operational programs) stored thereon that when executed by a computing device (e.g., processor), perform any of the methods disclosed herein (e.g., cause any of the ultrasound systems disclosed herein to perform one or more portions of any of the methods or acts disclosed herein).

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one skilled in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications can be made to the embodiments without departing from the scope of the present disclosure. For example, various operational steps, as well as components for carrying out operational steps, can be implemented in alternate ways depending upon the particular application or in consideration of any number of cost functions associated with the operation of the system e.g., one or more of the steps can be deleted, modified, or combined with other steps.

Additionally, as will be appreciated by one of ordinary skill in the art, principles of the present disclosure, including components, can be reflected in a computer program product on a computer-readable storage medium having computer-readable program code means embodied in the storage medium. Any tangible, non-transitory computer-readable storage medium can be utilized, including magnetic storage devices (hard disks, floppy disks, and the like), optical storage devices (CD-ROMs, DVDs, Blu-ray discs, and the like), flash memory, and/or the like. These computer program instructions can be loaded onto a general purpose computer, special purpose computer, or other programmable data processing apparatus to produce a machine, such that the instructions that execute on the computer or other programmable data processing apparatus create a means for implementing the functions specified. These computer program instructions can also be stored in a computer-readable memory that can direct a computer or other programmable data processing apparatus to function in a particular manner, such that the instructions stored in the computer-readable memory produce an article of manufacture, including implementing means that implement the function specified. The computer program instructions can also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the printing systems disclosed herein can be integrated in such a manner that the printing systems operate as a unique system configured specifically for function of printing (e.g., three-dimensional printing), and any associated computing devices of the printing systems operate as specific use computers for purposes of the claimed system, and not general use computers. In an embodiment, at least one associated computing device of the printing systems operates as specific use computers for purposes of the claimed system, and not general use computers. In an embodiment, at least one of the associated computing devices of the printing systems are hardwired with a specific ROM to instruct the at least one computing device. In an embodiment, one of skill in the art recognizes that the printing devices and printing systems effects an improvement at least in the technological field of three-dimensional printing.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A method for determining a presence of fluid in a body region, the method comprising:
    emitting ultrasound radiation at a frequency below about 15 MHz into a body region from an ultrasound transducer having a plurality of ultrasonic elements, wherein the ultrasound radiation has a dynamic range value that is less than about one third of a maximum dynamic range value of the ultrasound transducer, and wherein the maximum dynamic range value includes a maximum number of the plurality of ultrasonic elements in the ultrasonic transducer to individually receive returned ultrasound radiation;
    controlling one or more properties of the ultrasound radiation with a computing device operably coupled to the ultrasound transducer by actuating one or more operational programs having machine readable and executable instructions for controlling the ultrasound transducer, wherein the one or more operational programs include at least one B-line mode operational program and at least one non-B-line mode operational program, wherein the at least one B-line mode operational program includes machine readable and executable instructions for the plurality of ultrasonic elements for causing the ultrasound transducer to have a focal point about 1 mm to about 10 mm above a proximal surface of an interrogation site in the body region;
    receiving returned ultrasound radiation from the body region with the ultrasound transducer;
    automatically determining, via a machine vision system, a combination of parameters having a signal-to-noise ratio of at least 2 and a sharpness ratio of at least 0.2; and
    generating, with the computing device, an ultrasound echo map with the returned ultrasound radiation that includes one or more B-lines having the determined combination of parameters.

2. The method of claim 1, wherein:
    the at least one non-B-line mode operational program includes machine readable and executable instructions for the plurality of ultrasonic elements in the ultrasound transducer; and
    the at least one B-line mode operational program includes machine readable and executable instructions for the plurality of ultrasonic elements for only actuating less than about half of the ultrasonic elements of the non-B-line mode operational program.

3. The method of claim 2, wherein the at least one B-line mode operational program includes machine readable and executable instructions for the plurality of ultrasonic elements for only actuating about 4 to about 13 of the ultrasonic elements.

4. The method of claim 1, wherein:
    the at least one non-B-line mode operational program includes machine readable and executable instructions providing a power output value for the plurality of ultrasonic elements in the ultrasound transducer; and
    the at least one B-line mode operational program includes machine readable and executable instructions providing a power output value for the plurality of ultrasonic elements that is less than about half of the power output value of the at least one non-B-line mode operational program.

5. The method of claim 1, wherein:
    the at least one non-B-line mode operational program includes machine readable and executable instructions providing a first frequency value for the plurality of ultrasonic elements in the ultrasound transducer; and
    the at least one B-line mode operational program includes machine readable and executable instructions providing a second frequency value for the plurality of ultrasonic elements for causing the frequency of the at least one B-line mode operational program to be 85% or less of the first frequency value of the at least one non-B-line mode operational program.

6. The method of claim 5, wherein the at least one B-line mode operational program includes machine readable and executable instructions providing a second frequency value for the plurality of ultrasonic elements for causing the frequency of the at least one B-line mode operational program to be between about 3 MHz and about 10 MHz.

7. The method of claim 1, wherein the at least one B-line mode operational program includes machine readable and executable instructions for causing the ultrasound transducer to emit ultrasound radiation having a focused beam form in comparison to a single plane wave, multi-angle plane wave, weakly focused overlapping beam, or spatial compounding.

8. The method of claim 1, wherein the at least one B-line mode operational program includes machine readable and executable instructions for causing the ultrasound transducer to emit ultrasound radiation at a frequency of about 3 MHz to about 10 MHz to provide an ultrasound echo map having one or more B-lines that include a combination of a maximized signal-to-noise ratio and a maximized sharpness ratio.

9. The method of claim 1, wherein the at least one B-line mode operational program includes machine readable and executable instructions for causing one or more of:
    the ultrasound transducer to emit ultrasound radiation at a frequency of about 3 MHz to about 10 MHz to provide an ultrasound echo map having a B-line that includes a combination of a maximized signal-to-noise ratio and a maximized sharpness ratio;
    a power output value of a plurality of ultrasonic elements to operate at less than about one quarter of a maximum power output of the plurality of ultrasonic elements; and
    a number of the plurality of ultrasonic elements in the ultrasound transducer from emitting ultrasound radiation such that about 4 to about 13 of the plurality of the ultrasonic elements of the plurality of ultrasound elements emit ultrasound radiation.

* * * * *